(12) United States Patent
Spizzirri et al.

(10) Patent No.: US 11,511,002 B2
(45) Date of Patent: Nov. 29, 2022

(54) MODULAR ELECTROMAGNETIC HEATING SYSTEM

(71) Applicant: 915 Labs, LLC, Centennial, CO (US)

(72) Inventors: Lora N. Spizzirri, Inverness, IL (US);
Moses A. Magana, Topeka, KS (US);
Matthew J. Raider, Denver, CO (US)

(73) Assignee: 915 Labs, Inc., Denver, CO (US)

( * ) Notice: Subject to any disclaimer, the term of this patent is extended or adjusted under 35 U.S.C. 154(b) by 452 days.

(21) Appl. No.: 16/457,370

(22) Filed: Jun. 28, 2019

(65) Prior Publication Data

US 2020/0000947 A1 Jan. 2, 2020

Related U.S. Application Data

(60) Provisional application No. 62/692,202, filed on Jun. 29, 2018.

(51) Int. Cl.
| | |
|---|---|
| *A61L 2/00* | (2006.01) |
| *B01J 19/08* | (2006.01) |
| *A61L 2/04* | (2006.01) |
| *A61L 2/12* | (2006.01) |
| *A61L 2/26* | (2006.01) |
| *A23L 3/00* | (2006.01) |

(Continued)

(52) U.S. Cl.
CPC ............... *A61L 2/04* (2013.01); *A23L 3/001* (2013.01); *A23L 3/01* (2013.01); *A61L 2/12* (2013.01); *A61L 2/26* (2013.01); *H05B 6/802* (2013.01); *A23V 2002/00* (2013.01); *A61L 2202/11* (2013.01); *A61L 2202/122* (2013.01); *A61L 2202/123* (2013.01)

(58) Field of Classification Search
CPC . A23L 3/01; A61L 2/00; A61L 2/0064; A61L 2/12; B65B 55/00
USPC ................................................. 422/21, 186
See application file for complete search history.

(56) References Cited

U.S. PATENT DOCUMENTS

| | | |
|---|---|---|
| 5,750,966 A | 5/1998 | Ruozi |
| 6,323,473 B1 | 11/2001 | Yamamoto et al. |

(Continued)

OTHER PUBLICATIONS

International Searching Authority, International Search Report and Written Opinion, issued for International Application No. PCT/US2019/039931, dated Oct. 31, 2019 (13 pages).

(Continued)

*Primary Examiner* — Monzer R Chorbaji
(74) *Attorney, Agent, or Firm* — Polsinelli PC; David R. Mika

(57) ABSTRACT

Systems and methods including modular electromagnetic heating systems enable heating of articles using electromagnetic energy. The systems include a primary processing vessel equipped with electromagnetic energy launchers and fluid delivery systems to enable capable of preheating, heating, and cooling of the articles within the primary processing vessel. The primary processing vessel is further configured to be coupled to one or more upstream or downstream vessels such that portions of the preheating and/or heating functionality may instead be performed by the additional vessels. This flexibility enables scaling of the electromagnetic heating system between a relatively small (e.g., lab) scale system and a relatively large (e.g., production) scale system while minimizing capital expenditures and space requirements.

19 Claims, 12 Drawing Sheets

(51) Int. Cl.
    *H05B 6/80*         (2006.01)
    *A23L 3/01*         (2006.01)

(56)             References Cited

U.S. PATENT DOCUMENTS

| | | | |
|---|---|---|---|
| 2004/0131519 A1* | 7/2004 | Amedeo | A23L 3/04 |
| | | | 422/308 |
| 2005/0127068 A1 | 6/2005 | Tang et al. | |
| 2009/0283517 A1* | 11/2009 | Mackay | H05B 6/782 |
| | | | 219/700 |
| 2016/0183333 A1 | 6/2016 | Mohammed et al. | |
| 2017/0099706 A1 | 4/2017 | Kimrey, Jr. et al. | |
| 2017/0245528 A1* | 8/2017 | Hirschey | A23L 3/04 |
| 2018/0014559 A1 | 1/2018 | Tang et al. | |

OTHER PUBLICATIONS

Barbosa-Canovas, G.V. et al., Advanced retorting, microwave assisted thermal sterilization (MATS), and pressure assisted thermal sterilization (PATS) to process meat products, Meat Science, 98:420-434, 2014 (15 pages).

* cited by examiner

MODULAR ELECTROMAGNETIC HEATING SYSTEM

CROSS-REFERENCE TO RELATED APPLICATIONS

This application is related to and claims priority under 35 U.S.C. § 119(e) from U.S. patent application Ser. No. 62/692,202 filed Jun. 29, 2018, titled "PASTEURIZATION AND STERILIZATION SYSTEM WITH ENHANCED FLEXIBILITY", the entire contents of which are incorporated by reference for all purposes.

TECHNICAL FIELD

Aspects of the present disclosure relate to methods and systems for pasteurizing or sterilizing articles using electromagnetic radiation. Methods and systems described herein provide enhanced operational flexibility and efficiency when scaling a relatively smaller heating system to a relatively larger heating system. In one example, a vessel may be configured to perform various distinct pasteurization or sterilization operations, and additional vessels operably connected thereto in order to scale processing volume as demand arises.

BACKGROUND

Electromagnetic radiation based heating systems, which may be in the microwave spectrum, are conventionally used for pasteurizing and sterilizing various types of articles, including, for example, foodstuffs, beverages, and medical, dental, and pharmaceutical items and materials.

In general, differences in the design and operation of commercial-scale equipment versus lab- or pilot-scale equipment has made scaling these processes and systems complex and expensive, if not practically impossible. Thus, a need exists for a flexible heating system that can be efficiently scaled-up from small to large scale production, among other needs and advantages.

SUMMARY

In one aspect of the present disclosure, a method for pasteurizing or sterilizing a plurality of articles in an electromagnetic radiation heating system is provided. The method includes pasteurizing or sterilizing a first group of articles in a first processing vessel, the pasteurizing or sterilizing including preheating the first group of articles with a first warming liquid, heating the first group of articles using electromagnetic radiation energy, and cooling the first group of articles with a first cooling liquid. The method further includes attaching a second processing vessel to the first processing vessel to form a combined processing unit. The method also includes pasteurizing or sterilizing a second group of articles in the combined processing unit, the pasteurizing or sterilizing of the second group of articles including preheating the second group of articles with a second warming liquid, heating the second group of articles using electromagnetic radiation energy, and cooling the second group of articles with a second cooling liquid different from the first cooling liquid. During the pasteurizing or sterilizing of the second group of articles, at least a portion of the heating is performed in the first processing vessel and at least a portion of at least one of the preheating and the cooling is performed in the additional processing vessel.

In one implementation, the attaching step includes attaching the second processing vessel to one end of the first processing vessel and attaching a third processing vessel to the opposite end of the first processing vessel. In such implementations, during the pasteurizing or sterilizing of the second group of articles, at least a portion of the heating is performed in the first processing vessel, at least a portion of the preheating is performed in the second processing vessel, and at least a portion of the cooling is performed in the third processing vessel.

In another implementation, the first processing vessel includes a first end segment, a second end segment, and at least one launcher segment between the first and second end segments. The launcher segment includes pairs of launchers that discharge the electromagnetic radiation energy into the first processing vessel during the heating. In such implementations, the first and second end segments may not include any launchers.

In yet another implementation, the method may further include, prior to pasteurizing or sterilizing the first group of articles, loading the first group of articles in a first carrier and pasteurizing or sterilizing the first group of articles in the first carrier. The method may further include, prior to the pasteurizing or sterilizing of the second group of articles, loading the second group of articles into a second carrier and pasteurizing or sterilizing the second group of articles in the second carrier.

In another implementation, the first processing vessel is at least partially filled with a liquid during at least a portion of the heating of each of the first and second groups of articles.

In certain implementation, the pressure surrounding the first group of articles during each of preheating, heating, and cooling steps is within 10 psig of each of the other of the preheating, heating, and cooling steps.

In another aspect of the present disclosure, an electromagnetic heating system for pasteurizing or sterilizing a plurality of articles is provided. The system includes a processing vessel for receiving a carrier loaded with a plurality of articles. The processing vessel further includes a first end and a second end spaced apart from the first end defining a chamber therebetween. At least one of the first and said second ends of the processing vessel includes an opening configured for at least one of introducing the carrier into and removing the carrier out of the processing vessel. The processing vessel further includes a warm liquid inlet for introducing a warmed liquid into the chamber, a cool liquid inlet for introducing a cooled liquid into the chamber, a convey line for passing the carrier through at least a portion of the chamber, and two launchers for discharging electromagnetic energy into the chamber. The processing vessel is further configured to be a liquid-filled vessel for each of preheating the articles, heating the articles with electromagnetic energy, and cooling the articles.

In certain implementations, the launchers are two of a plurality of launchers for discharging electromagnetic energy into said chamber, the plurality of launchers including more than two launchers. In other implementations, the launchers are located on the same side of said processing vessel. In still other implementations the launchers are located on opposite sides of the processing vessel.

In some implementations, the processing vessel further includes a plurality of nozzles for discharging jets of pressurized liquid into the chamber during at least one of preheating and cooling of the carrier.

In other implementations, the convey line is configured to transport the articles in opposite first and second horizontal convey directions.

In certain implementations, the processing vessel includes a first end segment, a second end segment opposite the first end segment, and a launcher segment between the first end segment and the second end segment. In such implementations, the processing vessel is configured to perform a portion of the preheating in the first end segment, to perform a portion of the cooling in the second end segment, and to perform a portion of the heating in the launcher segment.

In still other implementations, the processing vessel may include at least two launcher segments.

In other implementations, the processing vessel is configured to be coupled to an additional vessel and, when coupled to the additional vessel, to disable at least one of preheating and cooling functions of the processing vessel.

In yet another aspect of the present disclosure, a method of heating articles is provided. The method includes conveying the articles through each of a first processing vessel and a second processing vessel. The first processing vessel includes each of a first preheating zone, a heating zone subsequent to the first preheating zone, and a first cooling zone subsequent to the heating zone while the second processing vessel includes one of a second preheating zone and a second cooling zone. The method includes preheating the articles in one of the first preheating zone and the second preheating zone by exposing the articles to a warmed liquid. The method further includes, while the articles are in the heating zone, directing electromagnetic energy from a plurality of launchers coupled to the first processing vessel into the first processing vessel to heat the articles and cooling the articles in one of the first cooling zone and the second cooling zone.

In certain implementations, the second processing vessel is coupled to the first processing vessel upstream of the first processing vessel such that the second processing vessel is isolatable from the first processing vessel. In such implementations, the second processing vessel includes a second preheating zone and the step of preheating the articles is performed in the second processing vessel.

In other implementations, the second processing vessel is coupled to the first processing vessel downstream of the first processing vessel such that the second processing vessel is isolatable from the first processing vessel. In such implementations, the second processing vessel includes a second cooling zone and the step of cooling the articles is performed in the second processing vessel.

In still another implementation, the method further includes conveying the articles through a third processing vessel. In such implementations, the second processing vessel is coupled to the first processing vessel upstream of the first processing vessel such that the second processing vessel is isolatable from the first processing vessel. The second processing vessel includes a second preheating zone and the step of preheating the articles is performed in the second processing vessel. Similarly, the third processing vessel is coupled to the first processing vessel downstream of the first processing vessel such that the third processing vessel is isolatable from the first processing vessel. The third processing vessel includes a second cooling zone and the step of cooling the articles is performed in the second processing vessel.

BRIEF DESCRIPTION OF THE DRAWINGS

The foregoing and other objects, features, and advantages of the present disclosure set forth herein will be apparent from the following description of particular implementations of those inventive concepts as illustrated in the accompanying drawings. It should be noted that the drawings are not necessarily to scale; however, emphasis instead is being placed on illustrating the principles of the inventive concepts. It is intended that the implementations and figures disclosed herein are to be considered illustrative rather than limiting.

DETAILED DESCRIPTION

Figure 1:
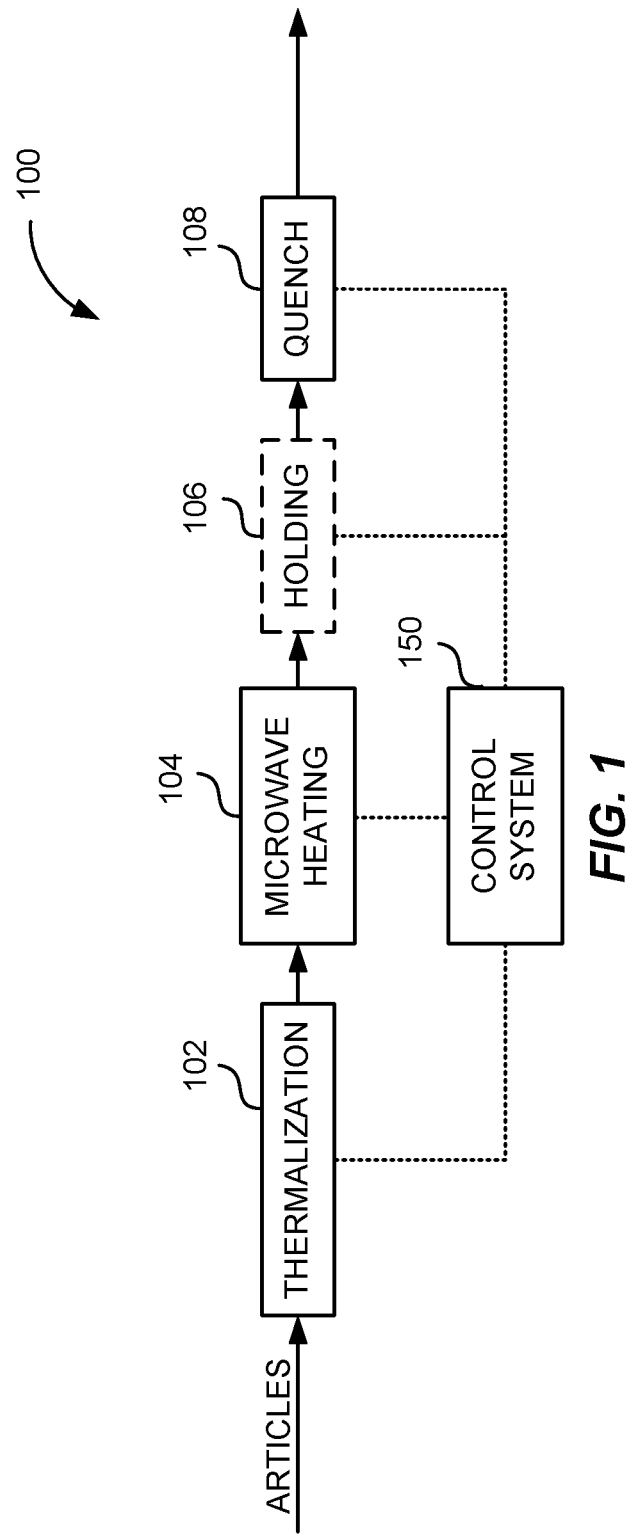
FIG. 1 is a process flow diagram depicting one implementation of a microwave heating system for heating one or more articles, particularly illustrating a system comprising a thermalization section, an electromagnetic heating section, an optional holding zone, and a quench zone.

According to implementations of the present disclosure, electromagnetic heating systems are provided that exhibit enhanced operational flexibility and permit rapid and efficient scale-up from small-scale (e.g., pilot-scale or lab-scale) up to commercial-scale production with minimal time and minimal capital outlay. Such heating systems begin as fully-operational single vessel units, and can be expanded to enhance production through the selective addition of further processing vessels designed to perform one or more functions originally carried out in the single vessel unit. Duplicate equipment is minimized since equipment from the smaller-scale unit is reused in the larger-scale system. Overall, systems and methods described herein are more flexible and streamline the entire process of commercial scale-up, resulting in significant time and cost savings.

In general, pasteurization involves the rapid heating of an item to a minimum temperature between about 80° C. and about 100° C., while sterilization involves heating the item to a minimum temperature between about 100° C. and about 140° C. In some cases, the processes and systems described herein may be configured for pasteurization, sterilization, or both pasteurization and sterilization. Examples of suitable types of items to be pasteurized and/or sterilized include, but are not limited to, packaged foodstuffs, beverages, medical instruments and fluids, dental instruments and fluids, veterinary fluids, and/or pharmaceutical fluids.

In general, pasteurization involves the rapid heating of an item to a minimum temperature between about 70° C. and about 100° C., while sterilization involves heating an item to a minimum temperature between about 100° C. and about 140° C. Examples of systems for sterilizing and pasteurizing using electromagnetic energy are described in U.S. Pat. No. 9,357,590, as well as U.S. Pat. No. 7,119,313, both which are incorporated herein by reference in their entirety to the extent not inconsistent with the present disclosure.

Systems and processes described herein may be configured for pasteurization, sterilization, or both pasteurization and sterilization. As described in more detail below, in some cases, pasteurization may be performed at lower temperatures and/or pressures and without a separate thermal equilibration period before or after the electromagnetic radiation heating, while sterilization may be performed at higher temperatures and/or pressures and can include a preheating step before the radiation heating step, as well as a holding or thermal equilibration stage after heating in order to hold the item at a temperature for sufficient time to achieve sterilization. In some embodiments, a single microwave system can be operationally flexible so that it is able to be selectively configured to pasteurize or sterilize various articles during different heating runs. The various operations involved in pasteurization or sterilization may initially be performed in a single vessel, and then operations distributed into one or more added vessels as the system is scaled. Examples of suitable types of items to be pasteurized and/or sterilized include, but are not limited to, packaged foodstuffs, beverages, medical instruments and fluids, dental instruments and fluids, veterinary fluids, and/or pharmaceutical fluids.

Turning now to FIG. 1, a schematic representation of the major steps and components in an electromagnetic heating system 100 of the present disclosure is depicted. The electromagnetic heating system 100 is operable to heat a plurality of articles in part using electromagnetic energy, such as microwave energy. As used herein, the term "microwave energy" generally refers to electromagnetic energy having a frequency between 300 MHz and 30 GHz. Although the present disclosure generally refers to microwave energy and As shown in FIG. 1, one or more articles can initially be introduced into a thermalization section 102 (also referred to herein as a pre-heat section), wherein the articles can be thermalized to a substantially uniform temperature. Once thermalized, the articles can then be introduced into an electromagnetic heating section 104. In electromagnetic heating section 104, the articles can be rapidly heated using electromagnetic energy, such as microwave energy, discharged into at least a portion of the heating section 104 by one or more launchers. The heated articles can then optionally be passed through a holding section 106, wherein the articles can be maintained at a constant temperature for a specified amount of time. Subsequently, the articles can then be passed to a cooling or quench section 108, wherein the temperature of the articles can be quickly reduced to a suitable handling temperature. Thereafter, the cooled articles can be removed from system 100 and further utilized.

According to one implementation of the present disclosure, each of the above-described thermalization, microwave heating, holding, and/or quench sections 102, 104, 106, and 108 can be defined within a single vessel, while, in another implementation, at least one of the above-described stages can be defined within one or more separate vessels.

In some cases, at least a portion of one or more of the steps shown in FIG. 1 can be performed while the articles are at least partially, or entirely, submerged in a liquid. For example, the articles may be at least about 50, at least about 60, at least about 70, at least about 80, at least about 90, or 100 percent submerged in a liquid during at least a portion of one or more of the above steps.

In at least certain implementations, at least one of the above-described steps (e.g., thermalization, heating, holding, cooling/quenching) can be carried out in a vessel that is at least partially filled with a liquid medium in which the articles being processed can be at least partially submerged. As used herein, the term "at least partially filled" denotes a configuration where at least 50 percent of the specified volume is filled with the liquid medium. In certain implementations of the present disclosure, "at least partially filled" volumes can be at least about 75 percent, at least about 90 percent, at least about 95 percent, or 100 percent full of the liquid medium.

When used, the liquid medium used may include any suitable type of liquid. The liquid medium may have a dielectric constant greater than the dielectric constant of air and, in one implementation, can have a dielectric constant similar to the dielectric constant of the articles being processed. Water (or liquid media comprising water) may be particularly suitable for systems used to heat edible and/or medical devices or articles. In one implementation, additives, such as, for example, oils, alcohols, glycols, and salts may optionally be added to the liquid medium to alter or enhance its physical properties (e.g., boiling point) during processing, if needed.

Electromagnetic heating system 100 can include at least one conveyance system (not shown) for transporting the articles through one or more of the processing sections described above. Examples of suitable conveyance systems can include, but are not limited to, plastic or rubber belt conveyors, chain conveyors, roller conveyors, flexible or multi-flexing conveyors, wire mesh conveyors, bucket conveyors, pneumatic conveyors, screw conveyors, trough or vibrating conveyors, and combinations thereof. The conveyance system can include any number of individual convey lines and can be arranged in any suitable manner within the process vessels. The conveyance system utilized by electromagnetic heating system 100 can be configured in a generally fixed position within the vessel or at least a portion of the system can be adjustable in a lateral or vertical direction.

The articles processed by the microwave heating system 100 may include packages of any suitable size and/or shape and may contain any food or beverage, any medical, dental, pharmaceutical, or veterinary fluid, or any instrument capable of being processed in a microwave heating system. Examples of suitable articles can include, but are not limited to, packaged foodstuffs such as, for example, fruits, vegetables, meats, pastas, pre-made meals, soups, stews, jams, and even beverages. The specific type of packaging is not limiting, but at least a portion of it must be at least partially microwave transparent in order to facilitate heating of the contents using microwave energy.

The articles can include individual packages each having, for example, a generally rectangular or prism-like shape. In some cases, the articles can have a top and a bottom and the top and bottom of each article can have different widths. For example, in some cases, the top can be wider than the bottom and top edge of each article may be longer and wider than the bottom edge. In other cases, the top may be narrower than the bottom when, for example, the article includes a flexible pouch. Specific types of articles can include, but are not limited to, flexible and semi-flexible pouches with or without spouts, cups, bottles, and other rigid or semi-rigid containers having circular, elliptical, or other cross-sectional shapes with or without lidding, including flexible lidding. The articles may be constructed of any material, including plastics, cellulosics, and other wave-transparent or semi-transparent materials.

As shown in FIG. 1, the articles introduced into electromagnetic heating system 100 are initially introduced into thermalization section 102, wherein the articles are thermalized to achieve a substantially uniform temperature. In one specific implementation, such preheating/thermalization is achieved by contacting the articles with a warmed fluid such that the articles achieve the substantially uniform temperature. For example and without limitation, in at least certain implementations of the present disclosure at least about 85 percent, at least about 90 percent, at least about 95 percent, at least about 97 percent, or at least about 99 percent of all the articles withdrawn from the thermalization section 102 have a temperature within about 5° C., within about 2° C., or within 1° C. of one another. As used herein, the terms "thermalize" and "preheat" generally refer to a step of temperature equilibration or equalization. In general, the thermalization step occurs prior to and in preparation for the electromagnetic heating step.

When the thermalization section 102 is at least partially filled with a liquid medium, the articles can be at least partially submerged in the liquid during the passing. The liquid medium in the thermalization section 102 can be warmer or cooler than the temperature of the articles passing therethrough. In some implementations and without limitation the liquid medium may have an average bulk temperature of at least about 30° C., at least about 35° C., at least about 40° C., at least about 45° C., at least about 50° C., at least about 55° C., or at least about 60° C. and/or not more than about 100° C., not more than about 95° C., not more than about 90° C., not more than about 85° C., not more than about 80° C., not more than about 75° C., not more than about 70° C., not more than about 65° C., or not more than about 60° C. The thermalization step occurs prior to and in preparation for the electromagnetic radiation heating step. Generally speaking, as the preheating step is performed through warm water circulated within the vessel, the amount of water within the vessel should be sufficient to submerge or substantially submerge the articles within the vessel.

The thermalization step can be carried out under ambient pressure or it may be carried out in a pressurized vessel. For example and without limitation, when pressurized, thermalization may be performed at a pressure of at least about 1 psig, at least about 2 psig, at least about 5 psig, or at least about 10 psig and/or not more than about 80 psig, not more than about 50 psig, not more than about 40 psig, or not more than about 25 psig. When the thermalization section 102 is liquid-filled and pressurized, the pressure may be in addition to any head pressure exerted by the liquid. Articles undergoing thermalization can have an average residence time in the thermalization section 102 of various durations. For example and without limitation, in certain implementations, the residence time may be at least about 1 minute, at least about 5 minutes, at least about 10 minutes and/or not more than about 60 minutes, not more than about 20 minutes, or not more than about 10 minutes.

The articles withdrawn from the thermalization section 102 can have differing average temperatures. In some embodiments, after the preheating step, the average temperature of the articles can be at least about 20° C., at least about 25° C., at least about 30° C., at least about 35° C., at least about 40° C., at least about 45° C., at least about 50° C., at least about 55° C., or at least about 60° C. and/or not more than about 100° C., not more than about 95° C., not more than about 90° C., not more than about 85° C., not more than about 80° C., not more than about 75° C., not more than about 70° C., not more than about 65° C., or not more than about 60° C. When the articles are being pasteurized, the temperature of the articles after the preheating step may be within various ranges suitable for pasteurization. For example and without limitation, when pasteurizing the articles, the temperature of the articles may be in the range of from about 30° C. to about 80° C., about 35 to about 75° C., or about 40 to about 70° C. Similarly, when the articles are being sterilized, the temperature of the articles after the preheating step may be within various ranges suitable for sterilization. For example and without limitation, when sterilizing the articles the temperature of the articles after the preheating step may be in the range of from about 50 to about 100° C., about 55 to about 95° C., or about 70 to about 90° C.

The articles exiting thermalization section 102 may subsequently be introduced into electromagnetic heating section 104. In electromagnetic heating section 104, the articles can be rapidly heated with a heating source that uses electromagnetic energy, such as microwave energy, discharged from one or more launchers. As previously noted, microwave energy may refer to electromagnetic energy having a frequency between about 300 MHz and 30 GHz. In one implementation, various configurations of the electromagnetic heating section 104 can utilize microwave energy having a frequency of about 915 MHz or a frequency of about 2.45 GHz, both of which have been generally designated as industrial microwave frequencies. Generally speaking, however, other wavelengths of electromagnetic energy may be employed in various possible scenarios. In certain implementations, the electromagnetic energy used in the electromagnetic heating section 104 may be polarized. In addition to microwave energy, the electromagnetic heating section 104 may optionally utilize one or more other heat sources such as, for example, conductive or convective heating or other conventional heating methods or devices. However, in at least some implementations of the present disclosure at least about 50, at least about 55, at least about 60, at least about 65, at least about 70, at least about 75, at least about 80, at least about 85, at least about 90, or at least about 95 percent of the energy used to heat the articles in the electromagnetic heating section 104 be electromagnetic energy.

The use of electromagnetic energy during the heating step permits rapid heating of the coldest portion of each article in order to rapidly achieve a minimum target temperature, such as a minimum pasteurization or sterilization temperature. In some embodiments, the minimum target temperature can be at least about 65° C., at least about 70° C., at least about 75°

C., at least about 80° C., at least about 85° C., at least about 90° C., at least about 95° C., at least about 100° C., at least about 105° C., at least about 110° C., at least about 115° C., at least about 120° C., at least about 121° C., at least about 122° C. and/or not more than about 130° C., not more than about 128° C., or not more than about 126° C. When the target temperature is a pasteurization target temperature, the target temperature may be at least about 65° C., at least about 70° C., at least about 75° C., at least about 80° C., at least about 85° C., or at least about 90° C. and/or not more than about 120° C., not more than about 115° C., or not more than about 110° C. When the target temperature is a sterilization temperature, it may be at least about 121° C., at least about 122° C. and/or not more than about 135° C., not more than about 130°, not more than about 128° C., or not more than about 126° C.

During the heating step, the articles may be heated to the target temperature in a relatively short period of time. This rapid heating helps minimize any damage or degradation of the articles caused by prolonged exposure to high temperatures, while still achieving the desired degree of pasteurization or sterilization. During the heating step, the articles may be heated for a period of at least about 5 seconds, at least about 20 seconds, at least about 60 seconds and/or not more than about 10 minutes, not more than about 8 minutes, not more than about 5 minutes, not more than about 3 minutes, not more than about 2 minutes, or not more than about 1 minute. The coldest temperature of each of the articles heated during the heating step can increase by at least about 20° C., at least about 30° C., at least about 40° C., at least about 50° C., at least about 75° C. and/or not more than about 150° C., not more than about 125° C., or not more than about 100° C.

When the heating step is carried out while the articles are at least partially submerged in a liquid, the average bulk temperature of the liquid may vary and, in some cases, can depend on the amount of energy discharged into the vessel. In some cases, the average temperature of the liquid in the vessel surrounding the articles or within which the articles are at least partially submerged can be at least about 70° C., at least about 75° C., at least about 80° C., at least about 85° C., at least about 90° C., at least about 95° C., at least about 100° C., at least about 105° C., at least about 110° C., at least about 115° C., or at least about 120° C. and/or not more than about 135° C., not more than about 132° C., not more than about 130° C., not more than about 127° C., or not more than about 125° C.

The heating step can be performed at approximately ambient pressure, or it may be performed at an elevated pressure above ambient. For example, in some cases, the articles may be heated under a pressure of at least 5 psig, at least about 10 psig, at least about 15 psig, or at least about 17 psig and/or not more than about 80 psig, not more than about 60 psig, not more than about 50 psig, or not more than about 40 psig. Generally speaking, pressure may be applied during the heating step to help avoid package bursting from steam that may be generated within a sealed package.

In some implementations, after the heating step, the heated articles may be subjected to a "hold" period, during which the minimum temperature of each of the articles is maintained at or above a certain minimum target temperature for a predetermined period of time. For example, in some embodiments, during the holding step, the temperature of the coldest part of each article can be held at a temperature at or above a predetermined minimum temperature. Although the predetermined minimum temperature may vary, in at least some specific implementations, the predetermined minimum temperature may be at least about 70° C., at least about 75° C., at least about 80° C., at least about 85° C., at least about 90° C., at least about 95° C., at least about 100° C., at least about 105° C., at least about 110° C., at least about 115° C., or at least about 120° C., at least about 121° C., at least about 122° C. and/or not more than about 130° C., not more than about 128° C., or not more than about 126° C. The predetermined period of time (or "holding period") may also vary; however in at least certain implementations, the holding period may be of at least about 2 minutes, at least about 4 minutes, at least about 5 minutes, or at least about 10 minutes and/or not more than about 20 minutes, not more than about 16 minutes, or not more than about 10 minutes. In other embodiments, the articles are cooled directly after the microwave heating step with a holding period of not more than about 2 minutes or not more than about 1 minute, or with no holding period at all. Holding may be performed in order to maintain the temperature of the item at an appropriate temperature for sterilization or pasteurization, and hold the temperature for whatever time is needed for the particular item or most likely collection of items, among other possible reasons.

After heating and, in some cases, after the holding step, the articles may be rapidly cooled via contact with a cooled liquid. During cooling, the external surface temperature of the articles may be reduced by varying amounts. For example, in certain implementations the external surface temperature of the articles may be reduced by at least about 30° C., at least about 40° C., at least about 50° C. and/or not more than about 100° C., not more than about 75° C., or not more than about 50° C. Such cooling may occur over varying time periods; however, in certain implementations the cooling time period may be at least about 1 minute, at least about 2 minutes, at least about 3 minutes and/or not more than about 10 minutes, not more than about 8 minutes, or not more than about 6 minutes. Any suitable liquid may be used in the cooling section 108, and the liquid may be similar to, or different than, the liquid used in the microwave heating section 104 and/or the holding section 106. After cooling, the average temperature of the articles may vary across applications; however, in at least certain implementations, the average temperature may be at least about 20° C., at least about 25° C., at least about 30° C. and/or not more than about 70° C., not more than about 60° C., or not more than about 50° C.

In some embodiments, such as, for example, when the articles are being sterilized, the pressure around the articles may be adjusted prior to the heating step and/or before the cooling step, or after at least a portion of the cooling step has been carried out. In one example, pressure may be reduced when the temperature of a package is a level where bursting is unlikely. When at least a portion of the preheating, heating, and/or cooling steps are performed at different pressures, the difference in pressure between one or more of these steps may vary; however, in certain implementations the difference may be at least about 5 psig, at least about 10 psig, or at least about 15 psig and/or not more than about 35 psig, not more than about 30 psig, not more than about 25 psig, or not more than about 20 psig. In other example implementations, each of the preheating, heating, and cooling steps may be performed at a pressure within about 5 psig, within about 3 psig, or within about 2 psig of one another. In a single vessel arrangement where various operations are performed within a single vessel, pressure may be controlled within the vessel depending on the step being performed within the vessel, and other possible conditions. In some cases, where additional vessels are coupled with an existing vessel and the various vessels may be performing different operations, pressure locks may be positioned between vessels so that items moving (e.g., being conveyed) from one vessel to the next are done while maintaining pressure within a given vessel, which may be different from adjacent vessels.

In some cases, the articles may be loaded into one or more carriers configured to secure the articles during at least one of the preheating, heating, holding (when used), and cooling steps described previously. Carriers may be used when, for example, all or a portion of these steps are performed when the articles are at least partially, or entirely, submerged in a liquid. Examples of suitable carriers possible for use in microwave heating systems described herein are provided in U.S. patent application Ser. No. 15/284,173, the entirety of which is incorporated herein by reference to the extent not inconsistent with the present disclosure. The vessel may include rail systems or other conveyance mechanisms to modularly interconnect with an adjacent vessel, and transport the carrier from one vessel to the next.

As illustrated in FIG. 1, operation of the various sections of the microwave heating system 100 may be controlled and facilitated by a control system 150. The control system 150 generally includes one or more computing devices adapted to communicate with components of one or more of the sections of the microwave heating system 100. Such communication may include receiving signals and data from sensors, switches, or other components of the microwave heating system 100 and/or transmitting signals, such as control signals, and data to components of the microwave heating system 100 such as, without limitation, actuators, heating elements, drives, lights, alarms, screens, and the like. The control system 150 may be configured to receive input from a user and to control operation of the microwave heating system 100, at least in part, in response to such input. Similarly, the control system 150 may be configured to at least partially control operation of the heating system 100 automatically.

Heating systems as discussed herein are configured to be scaled up or down while still providing consistent operation at a variety of production rates. For example, in some cases, the heating system may be a single vessel unit capable of pasteurizing or sterilizing articles on a relatively small scale. As used herein, the term "vessel" refers to a process chamber that is fluidly isolatable from an adjacent process chamber during operation of the unit. Although different steps may be performed in different areas or zones within a processing chamber, such areas or zones are not considered to be "vessels," as defined herein unless such areas or zones are fluidly isolatable during operation of the system.

One or more additional process vessels may be attached to an original single vessel unit in order to expand the production capacity of the system. Systems of the present invention may include one or more vessels of the same core structure, but may be configured, reconfigured or otherwise altered to function as preheating, heating, holding or cooling (or combinations thereof), which may differ from the function of the original vessel to increase production more efficiently. For example, the additional process vessels may be used for providing preheating and/or cooling, while the original vessel may continue to be used for heating. In such cases, carriers can be moved from a first new vessel configured for preheating to the original vessel configured for heating and then to the second new vessel configured for cooling. Various embodiments of suitable systems are described below with respect to FIGS. 2-6.

When a system includes a single vessel, each of the preheating, electromagnetic heating, holding, and cooling steps (whichever are applicable in the system arrangement) may be carried out in the same vessel. One example of such a system 200 is depicted schematically in FIG. 2. The system 200 depicted in FIG. 2 includes a single vessel 202 having two opposed ends 204A, 204B and defining a chamber 206 therebetween. At least one of the ends includes at least one opening (not shown) for introducing a carrier into and/or removing a carrier from the chamber. In some cases, the vessel 202 may include a single opening for introducing and removing the carrier from the chamber. In other cases, the vessel 202 may include an inlet opening for introducing the carrier into the chamber 206 at one end and an outlet opening for removing the carrier from the chamber 206 at the opposite end.

Figure 2:
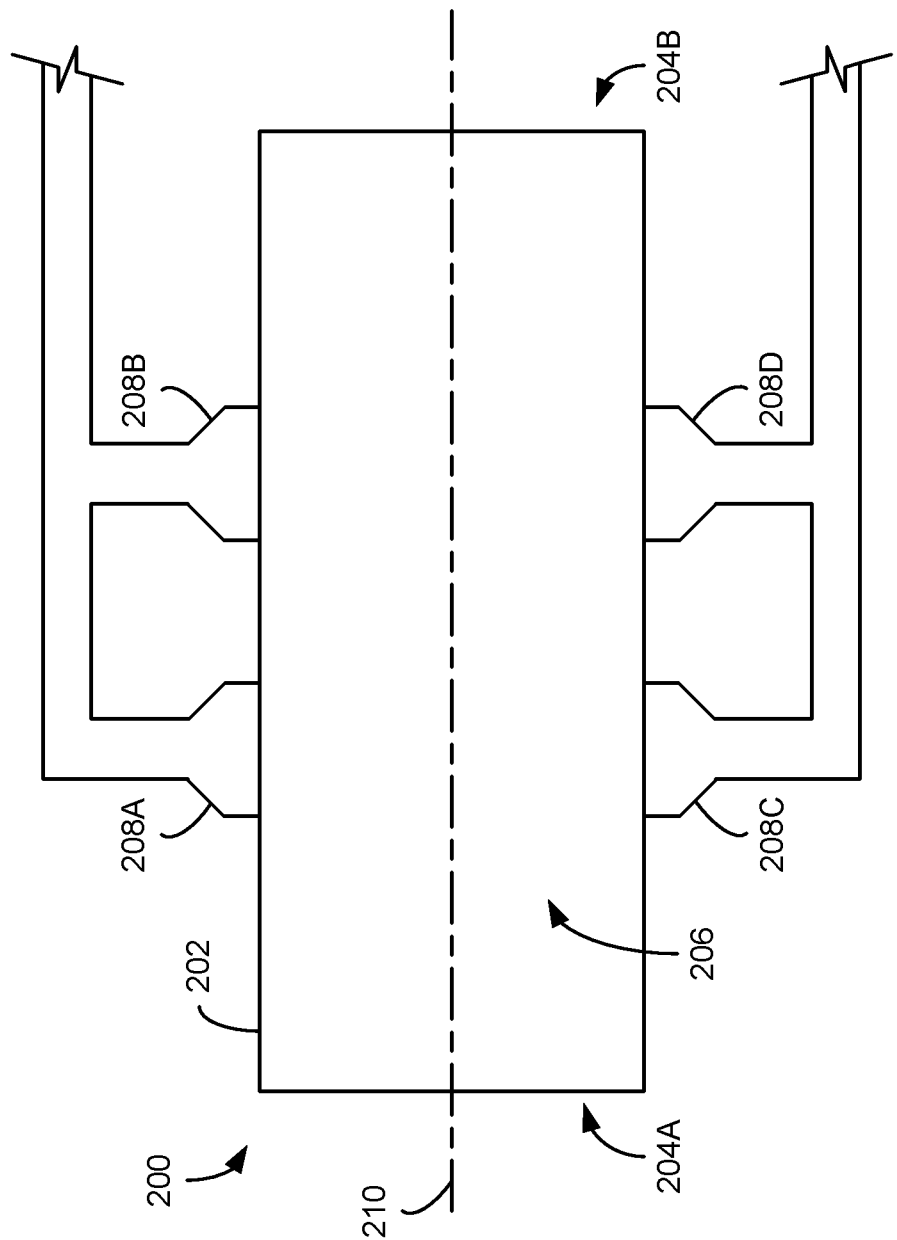
FIG. 2 is a schematic diagram of an electromagnetic heating system configured according to one implementation of the present disclosure including a single vessel within which each of the zones indicated in FIG. 1 may be implemented.

Additionally, the heating system 200 shown in FIG. 2 also includes a plurality of launchers 208A-D for discharging electromagnetic energy into the chamber. Generally speaking, a launcher is an assembly of components used to deliver electromagnetic energy (e.g., microwave energy) into the chamber 206. Any suitable number and arrangement of launchers can be used. For example and without limitation, the heating system 200 can include at least 2, at least 3, at least 4, at least 5, at least 6, at least 7, at least 8, at least 9, or at least 10 total launchers and/or not more than 50, not more than 40, not more than 30, not more than 20, not more than 18, not more than 16, not more than 14, or not more than 12 total launchers.

The system 200 may include at least two same-side launchers. As used herein, the term "same-side launchers" refers to two or more launchers positioned on generally the same side of the vessel 202. Two or more same-side launchers may be axially and/or laterally spaced from one another. As used herein, the term "axially spaced" denotes spacing in a direction parallel to the axis of elongation 210 of the vessel 202, while the term "laterally spaced" denotes spacing in a direction perpendicular to the axis of elongation 210 of the vessel 202. When a convey line is present within vessel 202, adjacent same-side launchers may be axially spaced from one another in a direction parallel to the convey direction and/or laterally spaced from one another in a direction perpendicular to the convey direction. To support the launchers, the vessel 202 may include one or more coupling structures (not shown) that allow for the launchers to be connected and/or disconnected from the vessel 202. Accordingly, the vessel 202 may include a sufficient number of coupling structures to support the number and position of the launchers connectable to the vessel 202. Similarly, a discrete segment may also include such coupling structures.

Additionally, or in the alternative, the heating system 200 may include at least two opposed launchers. As used herein, the term "opposed launchers" refers to launchers positioned on generally opposite sides of the vessel 202. Pairs of opposed launchers may include two oppositely facing launchers or two oppositely staggered launchers. As used herein with respect to opposed microwave launchers, the term "oppositely facing" denotes launchers whose central launch axes are substantially aligned with one another. As used herein with respect to opposed launchers, the term "oppositely staggered" denotes launchers whose central launch axes are not aligned. In at least some implementations the system 200 may include at least 2, at least 3, at least 4, at least 5, or 6 or more pairs of opposed launchers.

Each launcher can have any suitable configuration. For example, in some cases, each launcher may have a single, generally rectangular launch opening, while, in other cases, each launcher can include a single inlet and two or more spaced apart launch openings. Additionally, one or more of the launchers can be tilted launchers oriented to discharge energy into the vessel 202 at a launch tilt angle of from about 2° to about 15°. Additional examples of suitable types and configurations of launchers, particularly microwave launchers, are described in detail in U.S. Pat. No. 9,357,590, which is incorporated herein by reference in its entirety to the extent not inconsistent with the present disclosure. The coupling structure is suitable for the type of launcher used with the vessel.

Figure 3:
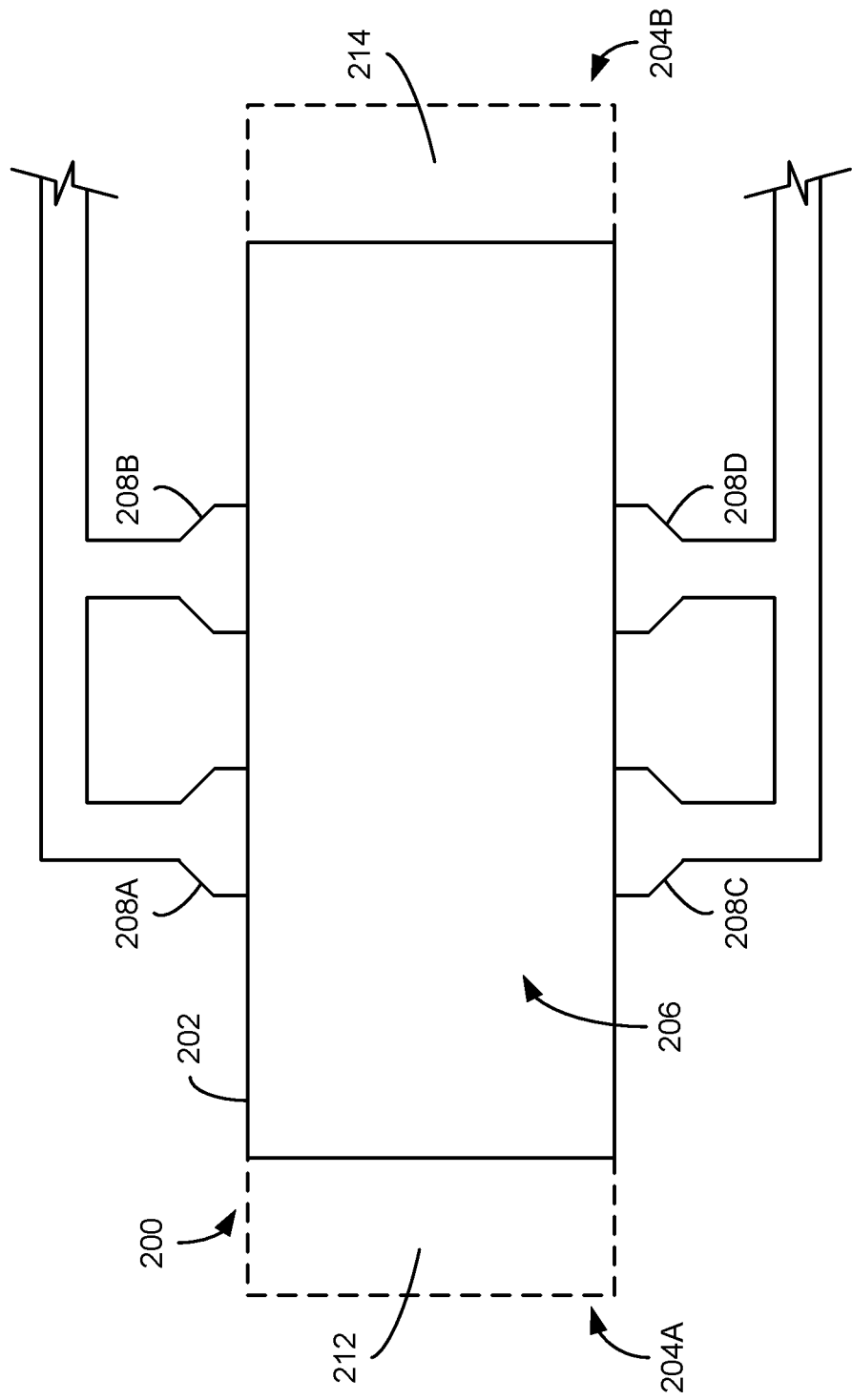
FIG. 3 is a second schematic illustration of the electromagnetic heating system of FIG. 2 including end segments that are set apart from an electromagnetic heating segment and within which preheating, holding, and/or cooling functions may be conducted.

Referring now to FIG. 3, another schematic illustration of the heating system 200 is provided. As shown in FIG. 3, the processing vessel 202 used in the single vessel heating system 200 may include a plurality of segments. As used herein, the term "segments" refers to areas of a vessel used to perform a certain function or portion of an overall step. Unlike vessels, segments are not fluidly isolatable from one another during operation of the system since no isolation devices, such as gate valves, doors, etc. are used between segments. Rather, the segments of a vessel are open to one another, with little or no restriction of the flow path therebetween, so that each segment maintains fluid flow communication with each of the other segments during operation of the vessel. For example, less than 20 percent, less than 15 percent, less than 10 percent, less than 5 percent, less than 2 percent, or less than 1 percent of the flow path between individual segments may be restricted during operation.

As shown in FIG. 3, the vessel 202 of the heating system 200 may include at least three segments, namely a first end segment 212, a second end segment 214, and at least one launcher segment 216 located between the first end segment 212 and the second end segment 214. In general, one of the end segments 212, 214 may be configured as an entrance segment to receive a carrier loaded with a plurality of articles through an inlet opening (not shown). Depending on the specific configuration of the vessel 202, the same end segment or the other end segment may be configured as an exit segment for facilitating removal of the loaded carrier from an outlet opening of the vessel (not shown).

The end segments 212, 214 of the vessel 202 do not include any launchers and none of the launchers of the heating system 200 are configured to discharge energy directly into either of the end segments 212, 214. Instead, the launchers 208A-D are configured to discharge energy into one or more launcher segments, such as launcher segment 216, as generally shown in FIG. 3. Each launcher segment can include any suitable number of launchers. For example, in certain implementations, each launcher segment may include at least 2, at least 3, at least 4, at least 5, at least 6, at least 7, or at least 8 individual launchers and/or not more than 12, not more than 10, or not more than 8 individual launchers. These launchers may be arranged as same-side and/or opposed launchers. The vessel 202 may include multiple launcher segments. For example, the vessel 202 may include at least 1, at least 2, at least 3, at least 4 and/or not more than 8, not more than 6, not more than 5, or not more than 4 total launcher segments between the end segments 212, 214.

In some cases, the total length of the launcher segments can make up a significant portion of the total length of the vessel 202, particularly when the vessel 202 includes a launcher segment, such as shown in FIGS. 2 and 3. For example, the ratio of the total length of the launcher segment(s) to the total length of the vessel 202 can be at least about 0.15:1, at least about 0.20:1, at least about 0.25:1, at least about 0.30:1, at least about 0.35:1, or at least about 0.40:1 and/or not more than about 0.75:1, not more than about 0.70:1, not more than about 0.65:1, not more than about 0.60:1, not more than about 0.55:1, not more than about 0.50:1, or not more than about 0.45:1. The total length of the launcher segment(s) may be measured from the leading flange of the first launcher segment to the trailing flange of the last launcher segment or, if no flanges are present, from the leading edge of the first launcher in the first launcher segment to the trailing edge of the last launcher in the last launcher segment.

Figure 4A:
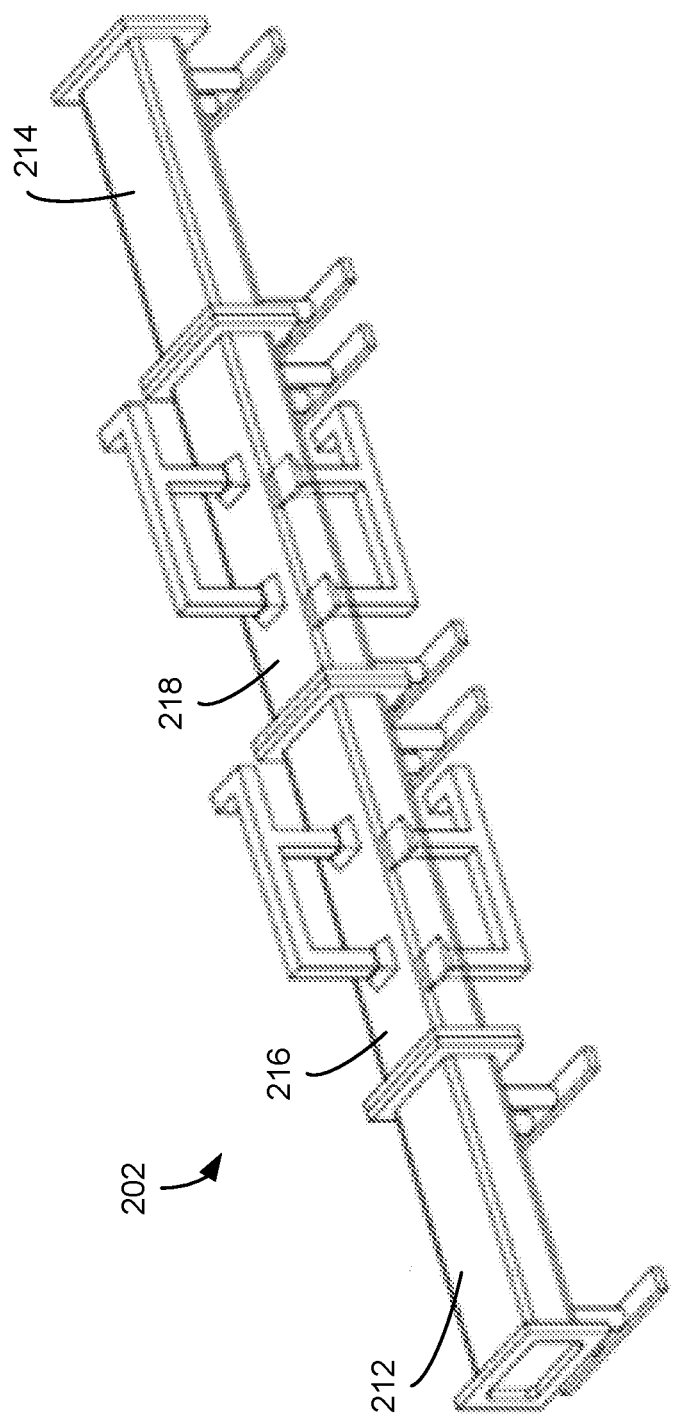
FIG. 4A is an isometric view of the electromagnetic heating system of FIG. 2 including multiple electromagnetic heating segments and rectangular end segments.
Figure 4B:
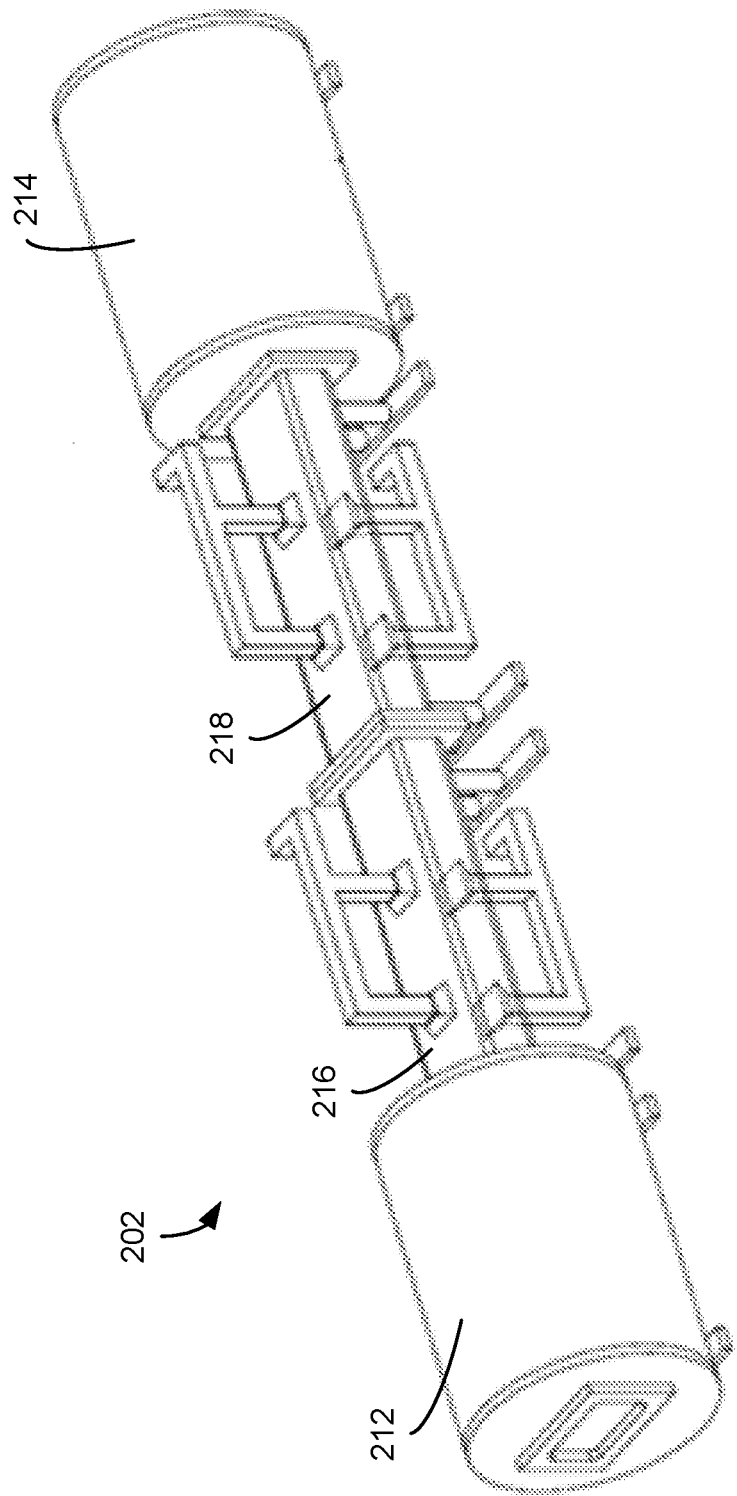
FIG. 4B is an isometric view of the electromagnetic heating system of FIG. 2 including multiple electromagnetic heating segments and circular end segments.

Each of the end segments and launcher segments can have any suitable cross-sectional shape. The cross-sectional shape of each type of segment can be the same or different. For example, in some cases, both the launcher segments and the end segments may have a generally rectangular cross-sectional shape. One example of such a configuration is shown in FIG. 4A. As illustrated in FIG. 4A, the vessel 202 includes two end segments 212, 214 and two launcher segments 216, 218, each having a generally rectangular cross-sectional shape. Alternatively, the launcher segments 216, 218 can have a generally rectangular cross-sectional shape, while the end segments may have a generally cylindrical or other cross-sectional shape. One example of such a configuration is shown in FIG. 4B, in which the vessel 202 includes two end segments 212, 214, each of which has a generally circular or cylindrical cross-sectional shape, and two launcher segments 216, 218, each of which has a generally rectangular cross-sectional shape.

One or more of the launcher segments may be configured to be independent of the others, so that each segment can be removably coupled to the end segments and/or adjacent launcher segments. Thus, one or more launcher segments can be added to or removed from the processing vessel between heating trials in order to provide an expanded or shortened processing vessel, in which further pasteurization or sterilization could be performed with more or fewer launchers. In addition to providing more or fewer launchers, such removability may also minimize downtime and further enhance the operational flexibility of the system.

Figure 5:
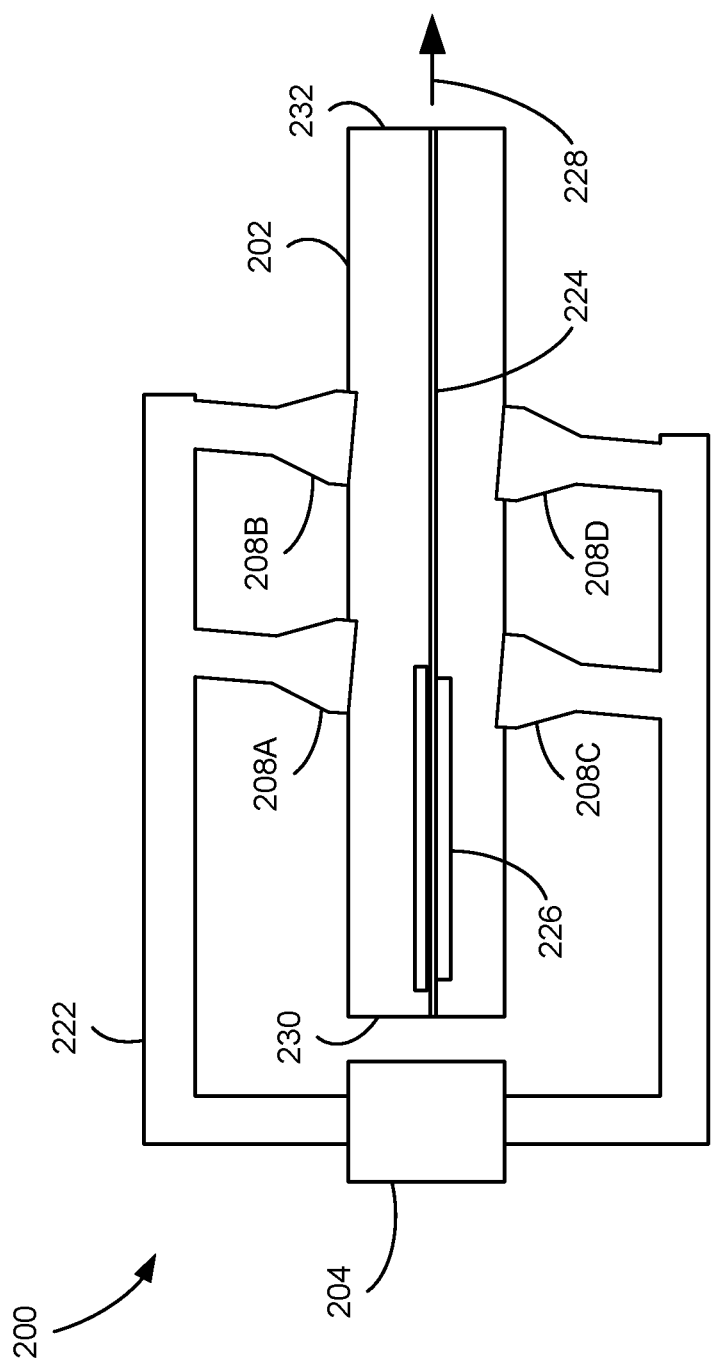
FIG. 5 is a third schematic illustration of the electromagnetic heating system of FIG. 2 including an electromagnetic energy distribution system.

Turning now to FIG. 5, another schematic view of the vessel 202 of the heating system 200 that particularly illustrates the electromagnetic energy distribution system of the heating system 200. FIG. 5 is discussed with particular reference to a microwave heating system but it should be recognized that it is applicable to electromagnetic radiation heating more generally.

The heating system 200 shown in FIG. 5 generally includes the vessel 202, at least one microwave generator 220 for generating microwave energy, and a microwave distribution system 222 for directing at least a portion of the microwave energy from the generator 220 to the vessel 202. The microwave distribution system 222 is shown as including four launchers 208A-D for directing microwave energy from the microwave distribution system 222 into the vessel 202.

Additionally, the heating system 200 includes at least one convey line 224 for transporting one or more carriers 226 within the vessel 202. Examples of suitable types of convey lines can include, but are not limited to, plastic or rubber belt conveyors, chain conveyors, roller conveyors, flexible or multi-flexing conveyors, wire mesh conveyors, bucket conveyors, pneumatic conveyors, screw conveyors, trough or vibrating conveyors, and combinations thereof. Any suitable number of individual convey lines can be used within the vessel 202, and the convey line 224 or lines may be arranged in any suitable manner within the vessels 202.

As generally shown in FIG. 5, the convey line 224 may be configured to move the carriers 226 in a convey direction 228 that is generally parallel to the axis of elongation of the vessel. In some cases, the convey line 224 may be configured to pass the carriers 226 in a single forward direction away from an inlet 230 of the vessel 202 and through the vessel 202 to an outlet 232. In other cases, the convey line 224 may be configured to pass the carriers 226 alternatively in a forward direction and a backward direction opposite the forward direction. The convey line 224 may be configured to move the carriers 226 relatively continuously through the vessel 202 during at least a portion of the preheating, heating, holding, and/or cooling stages, depending on the arrangement of the heating system 200. Alternatively, or in addition, the convey line 224 may be configured to stop carriers within a certain portion or segment of the vessel 502 during at least a portion of the preheating, heating, holding, and/or cooling steps. In some cases, carriers, may be alternately in motion and stopped for various portions of the pasteurization or sterilization process.

The convey line 224 may be configured to transport the carriers 226 through the vessel 202 in a single-stack configuration, as generally illustrated in FIG. 5. That is, the convey line 224 may transport the carriers 226 through the vessel 202 singly, with no carriers vertically stacked above or below a given carrier. All (or substantially all) of the convey path along which the carriers 226 are moved by the convey line 224 or the convey line 224 itself may be horizontal. For example, in certain implementations and without limitation, at least about 75 percent, at least about 80 percent, at least about 85 percent, at least about 90 percent, at least about 95 percent, at least about 97 percent, or all of the convey line 224 or path may be within about 10° of horizontal. In some cases, all (or substantially all) of the convey path may be horizontal. Consequently, none, or substantially none, of the convey path may be vertical. For example, in the foregoing examples and without limitation, not more than 25 percent, not more than 20 percent, not more than 15 percent, not more than 10 percent, not more than 5 percent, not more than 3 percent, or none of the convey path or line may be within about 10° of vertical. In some cases, none (or substantially none) of the convey line or path may be vertical.

Figure 6:
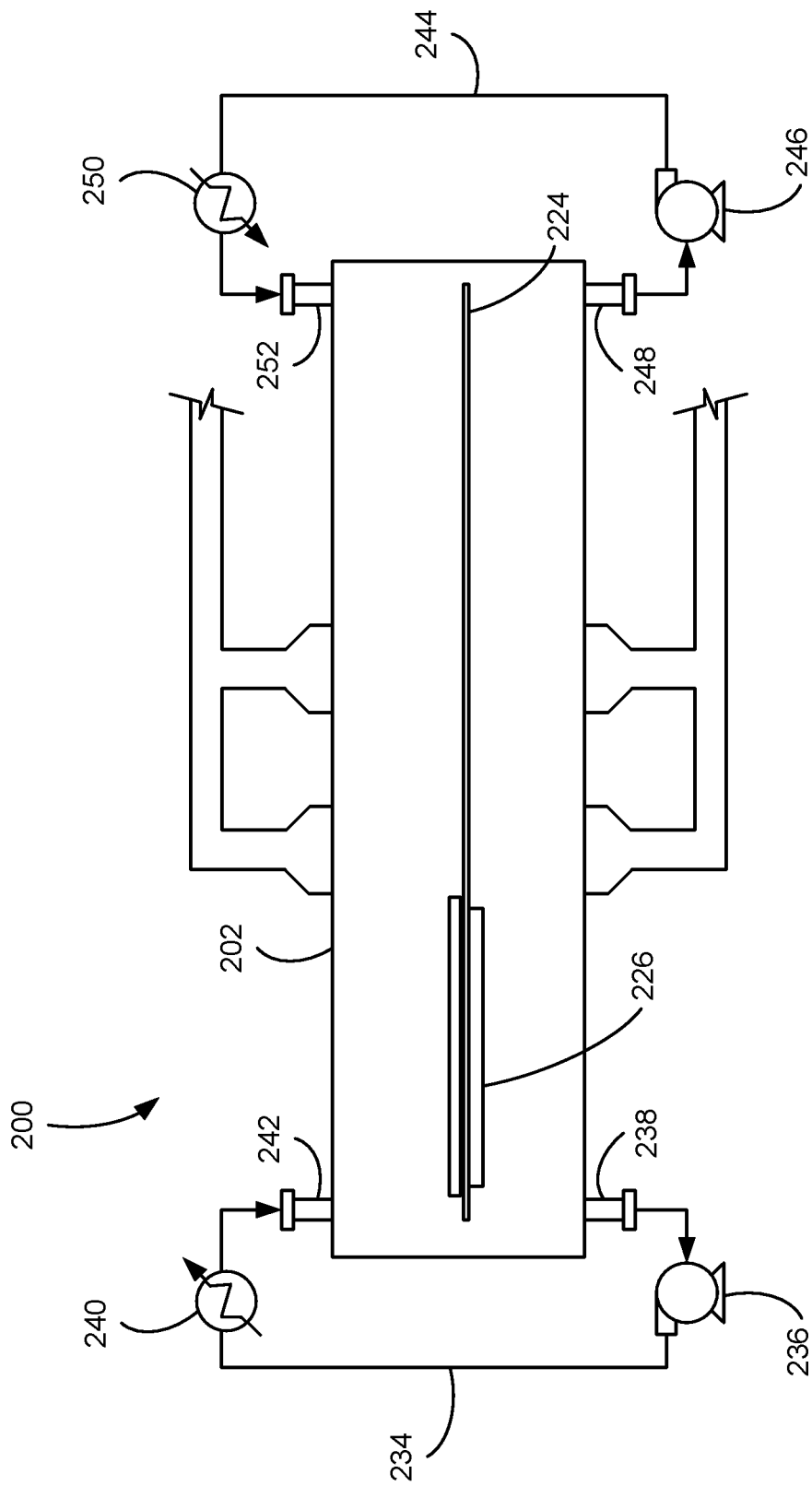
FIG. 6 is a fourth schematic illustration of the electromagnetic heating system of FIG. 2 including each of heating and cooling loops for providing heated and cooled liquid to the electromagnetic heating system.

Referring now to FIG. 6, an alternative schematic illustration of the heating system 200 is provided. The heating system 200 includes the processing vessel 202 and further illustrates a temperature control system for delivering temperature controlled liquid into the vessel 202. More specifically, the heating system 200, as shown in FIG. 6, includes a heating loop 234 for delivering a warmed liquid to the vessel 202 and a cooling loop 244 for delivering a cooled liquid to the vessel 202. Although shown in FIG. 6 as including separate loops, it is also possible that one or more elements of each loop 234, 244 may be integrated to provide a combined loop capable of delivering warmed or cooled liquid to the vessel. Although the temperature differential between the warmed and cooled liquid may vary, in some specific cases, the cooled liquid is at least about 5° C., at least about 10° C., at least about 15° C., at least about 20° C., or at least about 25° C. cooler than the warmed liquid.

As shown in FIG. 6, the heating loop 234 includes a pump 236 for circulating liquid withdrawn from a liquid outlet 238 to a heater 240. In one specific example, the heater 240 warms the liquid via indirect heat exchange with steam or another hot heat transfer fluid, although any suitable method of heating the liquid may be implemented. The warmed liquid can then be returned to the vessel 202 via a warmed liquid inlet 242. Similarly, the cooling loop 244 shown in FIG. 6 includes a pump 246 for circulating liquid withdrawn from a second liquid outlet 248 of the vessel 202 to a cooler 250, wherein the liquid is cooled. It should be appreciated that in certain implementations, the vessel 202 may include only one outlet such that the liquid outlet 238 associated with the heating loop 234 and the liquid outlet 248 associated with the cooling loop are one in the same. In such implementations, further components for diverting fluid to the heating loop 234 and the cooling loop 244 may be included downstream of the common outlet. In one specific example, the cooler 250 cools the liquid via indirect heat exchange with cooling water or other cold heat transfer fluid, although any suitable method of cooling the liquid may be implemented. The resulting cooled liquid can be returned to the vessel 202 via a cooled liquid inlet 252. As generally shown in FIG. 6, the warmed liquid inlet 252 and the cooled liquid inlet 242 may be located near opposite ends of the vessel 202, but are generally configured to facilitate introduction of warmed or cooled liquid into the same vessel including the microwave launchers. Thus, the vessel 202 may preheat using warm water, pasteurize or sterilize using warm water and microwave energy, hold using warm water, and cool using cool water, in one possible example.

In certain implementations, the heating loop 234 may generally be operated during the preheating, heating, and, when applicable, holding steps of the pasteurization or sterilization process, while the cooling loop 244 may be operated mainly during the cooling step. However, the absolute and relative flow rates and/or temperatures of the warmed and cooled liquid may be adjusted at any time during any step of the process in order to control the temperature of the liquid surrounding the articles.

Figure 7:
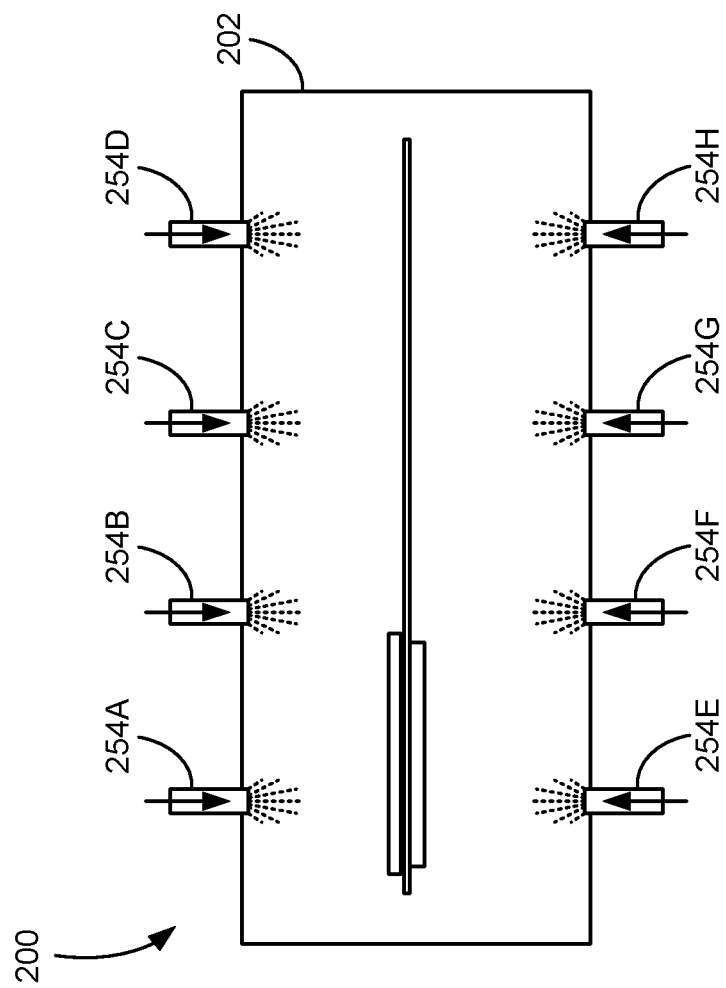
FIG. 7 is a fifth schematic illustration of the electromagnetic heating system of FIG. 2 and illustrating a vessel of the system having multiple nozzles for directing fluid into the vessel and towards articles being transported and heated by the system.

In some cases, heating systems in accordance with the present disclosure may further include one or more nozzles for discharging jets of pressurized fluid toward articles within the vessel during at least a portion of the preheating, heating, holding (if applicable), or cooling steps of the process. For example, FIG. 7 is an additional schematic illustration of the heating system 200 and, in particular a longitudinal cross-section of the vessel 202. As shown in FIG. 7, the heating system 200 may include a fluid discharge system including a plurality of nozzles 254A-H coupled to and adapted to discharge fluid into the vessel 202.

The nozzles 254A-H may be arranged in any suitable configuration and, in some cases, may be located at one or more areas along the perimeter of the vessel 202. Although shown in FIG. 7 section as being located at the top and bottom portions of the vessel 202, it should be understood that one or more nozzles may also be spaced apart along the lateral cross-section of the vessel, configured to discharge jets of pressurized fluid toward the articles and the axis of elongation of the vessel.

Similarly to the launcher couplings, the vessel 202 may include connection points for hosing and nozzles to be connected and removed depending on the configuration of the vessel 202, and further may be added or removed should the vessel 202 be repurposed when new vessels are added. When the vessel 202 comprises multiple segments, as discussed previously, one or more nozzles may be located in different segments. For example, in some cases, one or both of the end segments may include at least 1, at least 2, at least 3, at least 4, at least 5, at least 6, at least 7, at least 8, or 9 or more nozzles, while the launcher segments may include not more than 5, not more than 4, not more than 3, not more than 2, not more than 1, or no nozzles. Any type of fluid may be discharged from the nozzles and one or more nozzles may be configured to discharge a different fluid than one or more of the other nozzles. For example, in some cases, a portion of the nozzles in one end segment may be configured to discharge streams of pressurized warmed liquid into that segment, while the other end segment may include one or more nozzles configured to discharge streams of pressurized cooled liquid into that segment. In some cases, both end segments may include nozzles configured to discharge both warmed and cooled liquid into those segments, albeit not at the same time.

Operation of heating systems in accordance with the present disclosure and including a single processing vessel will now be described in detail, with collective reference to the heating system 200 and its components as illustrated in FIGS. 2 through 7. First, an empty carrier may be loaded with a plurality of different articles. The articles may include packages of any suitable size and/or shape and may contain any food or beverage, any medical, dental, pharmaceutical or veterinary fluid, or any instrument capable of being processed in an electromagnetic radiation heating system. Examples of suitable articles can include, but are not limited to, packaged foodstuffs such as, for example, fruits, vegetables, meats, pastas, pre-made meals, soups, stews, jams, and even beverages. The specific type of packaging is not limited, but at least a portion of it must be at least partially microwave transparent to facilitate heating of the contents using radiated energy such as microwave energy.

Next, the loaded carrier may be introduced into the vessel 202 via the inlet 230. In some cases, the vessel 202 may be configured to hold not more than 5 carriers at the same time. Alternatively, the vessel 202 may be configured to hold 3 or less, 2 or less, or only 1 carrier at a time during processing. However, the initial configuration of the vessel 202 may be scaled appropriately to hold other numbers of carriers, to stack carriers, and/or to position carriers side-by-side. As the heating system 200 is scaled up, its capacity for processing additional carriers may be increased.

Once in the vessel 202, the articles loaded in the carrier may be preheated via contact with a warmed liquid. The contact may include spraying the articles with jets of pressurized liquid (such as pressurized jets discharged into the vessel 202 by nozzles 254A-H), submerging the articles in a warmed liquid (such as a warmed liquid bath maintained using the heating loop 234), or both spraying and submerging the articles. When the contacting includes both spraying and submerging, at least a portion of the spraying and submerging can occur simultaneously. In other cases, the spraying of the articles may be stopped before the submerging begins.

As introduced above, spraying and water submersion is controlled by the nozzles 254A-H and attendant feed lines (not shown), control of the pump 236 and heater 240 of the heating loop 234, and similar systems. Among other things, the temperature of the warmed liquid within the vessel 202 can be controlled by adjusting at least one of the flow rate of the warmed liquid, the temperature of the warmed liquid, the flow rate of the cooled liquid, the temperature of the cooled liquid, the relative flow rates (or difference in flow rates) between the warmed and cooled liquids, and the relative temperatures (or differences in temperature) between the warmed and cooled liquids. In certain implementations, one or more of these parameters may be adjusted to achieve a preheating liquid temperature to preheat the articles in the carrier prior to heating using electromagnetic energy. For example and without limitation, the foregoing parameters may be used to preheat the articles to a temperature of at least about 30° C., at least about 35° C., at least about 40° C., at least about 45° C., at least about 50° C., at least about 55° C., or at least about 60° C. and/or not more than about 100° C., not more than about 95° C., not more than about 90° C., not more than about 85° C., not more than about 80° C., not more than about 75° C., not more than about 70° C., not more than about 65° C., or not more than about 60° C.

In some cases, the carrier may remain stationary during at least a portion of the preheating step, while, in other cases, the carrier may be moved along the convey line 224 during preheating. When in motion, the carrier may move through the vessel 202 in a forward and backward direction along the convey line. 224 In some cases, the carrier may be stationary during a portion of the preheating (such as, for example, when the articles are being sprayed with the warmed liquid) and may move during another portion of the preheating (such as, for example, when the articles are not being sprayed).

Once the articles have achieved a substantially uniform temperature, the articles may then be subjected to the pasteurization or sterilization heating step, as described above. During the heating step, the carrier may be moved in at least one convey direction past one or more of the launchers, which discharge energy, such as microwave energy, toward the articles in the vessel. In some cases, the carrier may pass back and forth through the vessel passing by each of the launchers one or more times. One example of a possible "back-and-forth" pattern of carrier movement is described in detail in U.S. patent application Ser Ser. No. 15/921,921, which is incorporated herein by reference in its entirety to the extent not inconsistent with the present disclosure.

After passing by one or more of the launchers 208a-d, the articles in the carrier may be exposed to a "dwell" time, in which the energy discharged is stopped (or reduced to a minimum of about 5 kW or less, about 2 kW or less, or about 1 kW or less) while the articles are permitted to thermally equilibrate. The carriers may or may not be in motion for all or a part of each dwell time. Although the dwell time may vary, in certain specific implementations the dwell time may be at least about 30 seconds, at least about 1 minute, at least about 2 minutes, or at least about 5 minutes and/or not more than about 10 minutes, not more than about 8 minutes, or not more than about 5 minutes. Dwell times may be alternated with periods of energy discharge until a target temperature is achieved.

During the heating step, the temperature of the liquid surrounding the articles within the vessel 202 may be controlled by adjusting the absolute and/or relative flow rate of the warmed and/or cooled liquid introduced into the vessel 202 in a manner similar to that described previously with respect to the preheating step. During the heating step, the temperature of the liquid may vary; however in at least certain non-limiting examples, the temperature of the liquid can be at least about 65° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 121° C., at least about 122° C. and/or not more than about 130° C., not more than about 128° C., or not more than about 126° C. In some cases, during electromagnetic heating, the temperature of the liquid may be maintained at a temperature that is at least about 1, at least about 2, at least about 5, or at least about 8° C. and/or not more than about 20, not more than about 15, not more than about 10, or not more than about 8° C. cooler than the target temperature of the items in the carrier or carriers.

In some cases, particularly when the articles being heated are being sterilized or pasteurized, the carriers may be subjected to a holding step after the heating step is complete. During one example holding step, less than about 5 kW of microwave energy (including no microwave energy) is discharged into the vessel and the temperature of the coldest portion of each article may be held at or above a minimum target temperature for a holding period. The carrier may move back and forth in the vessel 202 during all or a portion of the holding period, or the carrier may be held stationary for all or a portion of the holding period. Additionally, in some cases, jets of pressurized fluid may be discharged toward the articles (e.g., using nozzles 254A-H) during the holding period. In other cases, no jets are used and/or the articles may instead be submerged in a liquid bath. In applications utilizing jests of pressurized fluid, the articles may be sprayed to optimize heat exchange and maintenance of the temperature of the articles, and control is achieved by altering the temperature, pressure, and/or flow of the liquid from the nozzles 254A-H.

After the holding step (or after the heating step if the holding step is omitted), the articles may be exposed to a cooling stage to reduce their temperature. During cooling, the carrier may be stationary, it may move, or it may be stationary for some time and move for some time.

In certain implementations, the cooling step may include submerging the articles in a liquid and the temperature of the liquid used to cool the articles during the cooling step may be controlled using the heating and/or cooling loops 234, 244 as described in detail previously in the context of FIG. 6. In contrast to larger-scale facilities which employ isolated preheating, heating, and cooling zones, the preheating, heating, and cooling steps discussed herein may be performed in a single vessel with all segments being open to all other segments. As a result, when cooling water is introduced into the vessel 202 during the cooling step, the temperature of the liquid in the preheating and/or heating zones may also decrease. For example, such decrease may by at least about 5° C., at least about 10° C., at least about 15° C., or at least about 20° C. during the cooling step. In some cases, the difference between the minimum and maximum temperatures of the liquid medium within the vessel 202 is maintained within a specific range. For example, in one implementation, the different between the maximum and minimum temperatures of the liquid medium throughout the vessel 202 may be less than about 20° C. In other cases, temperature gradients may exist such that the difference between the minimum and maximum temperature of the liquid medium can be at least about 20° C. during at least a portion of the pasteurizing or sterilizing. A combination of submersion and spraying may be used for the cooling operations.

After cooling, the pasteurized or sterilized articles may be removed from the vessel 202. Articles removed from the vessel may exhibit a desired level of microbial lethality in order to be pasteurized or sterilized to a desired degree. For example and without limitation, when the articles are sterilized, the coldest portions of each article can achieve a minimum microbial lethality (F0) of *Clostridium botulinum*, measured at 250° F. (121.1° C.) with a z value of 18° F., of at least about 1 minute, at least about 1.5 minutes, at least about 1.75 minutes, at least about 2 minutes, at least about 2.25 minutes, at least about 2.5 minutes, at least about 2.75 minutes, at least about 3 minutes, at least about 3.25 minutes, or at least about 3.5 minutes and/or not more than about 10 minutes, not more than about 8 minutes, not more than about 6 minutes, not more than about 4 minutes, not more than about 3.75 minutes, not more than about 3.5 minutes, not more than about 3.25 minutes, not more than about 3 minutes, not more than about 2.75 minutes, not more than about 2.5 minutes, not more than about 2.25 minutes, or not more than about 2 minutes, measured according to ASTM F-1168-88(1994).

Similarly, for example and without limitation, when the articles are pasteurized, the coldest portion of each article can achieve a microbial lethality (F) of *Salmonella* or *Escherichia coli* (depending on the food being pasteurized), measured at 90° C. with a z value of 6° C. of at least about 5 minutes, at least about 5.5 minutes, at least about 6 minutes, at least about 6.5 minutes, at least about 7 minutes, at least about 7.5 minutes, at least about 8 minutes, at least about 8.5 minutes, at least about 9 minutes, at least about 9.5 minutes, at least about 10 minutes, at least about 10.5 minutes, at least about 11 minutes, or at least about 11.5 minutes. Alternatively, or in addition, the microbial lethality of *Salmonella* or *E. coli* can be not more than about 20 minutes, not more than about 19 minutes, not more than about 18 minutes, not more than about 17 minutes, or not more than about 16 minutes, measured according to ASTM F-1168-88(1994).

When processed in a single vessel as described above, each of the carriers in the vessel remains in a single stacked configuration during substantially all of the preheating, heating, holding (if applicable), and cooling steps. For example, each carrier remains in a single stacked configuration for at least about 85, at least about 90, at least about 95, or all of the preheating, heating, holding (if applicable), and cooling steps. Additionally, the carriers also travel in a substantially horizontal convey path, as described previously, and therefore, remain at generally the same vertical elevation for each of the preheating, heating, holding (if applicable), and cooling steps. For example, in some cases, the carriers stay within 5 feet, within 3 feet, within 2 feet, or within 1 foot of the same vertical elevation for the entire pasteurization or sterilization process. This is in contrast to some commercial systems in which articles are moved vertically.

The single vessel microwave heating system described herein may be suitable for smaller scale production, such as, for example, lab- or pilot-scale production. For example, in some cases, single vessel systems may be configured for an overall production rate of not more than about 25, not more than about 20, not more than about 15, not more than about 10, or not more than about 5 packages per minute. In some cases, the total volume of the vessel may be at least about 50, at least about 100, at least about 150, at least about 200, or at least about 250 cubic feet and/or not more than about 500, not more than about 450, not more than about 400, not more than about 350, not more than about 300, or not more than about 275 cubic feet.

According to various possible embodiments, the overall production rate of the heating system can be increased by, for example, attaching at least one additional vessel to the single vessel described previously to provide a combined processing unit. The combined processing unit can then be utilized for further pasteurization or sterilization of articles, with a portion of the process being performed in the original single vessel and a portion of the process being performed in the newly-added vessel. For example, the new vessel may be used for at least a portion of the preheating and/or cooling steps, while the heating step may be carried out in the original single vessel. Other configurations are possible and additional details of several implementations are discussed in further detail below.

When at least one additional processing vessel is attached to the original processing vessel, the attachment can be carried out in any suitable manner. For example, the vessels may be attached by flanges, or may be welded together. The vessels may be separated by a gate valve or a pressure lock (as described in U.S. Pat. No. 9,357,590), or may be otherwise fluidly isolatable from one another. In some cases, each isolation device used between the vessels may be configured to restrict some percentage of the flow path between the vessels such as at least about 40, at least about 45, at least about 50, at least about 55, at least about 60, at least about 65, at least about 70, at least about 75, at least about 80, at least about 85, at least about 90, or at least about 95, or all (i.e., 100%) of the flow path between the vessels.

Figure 8:
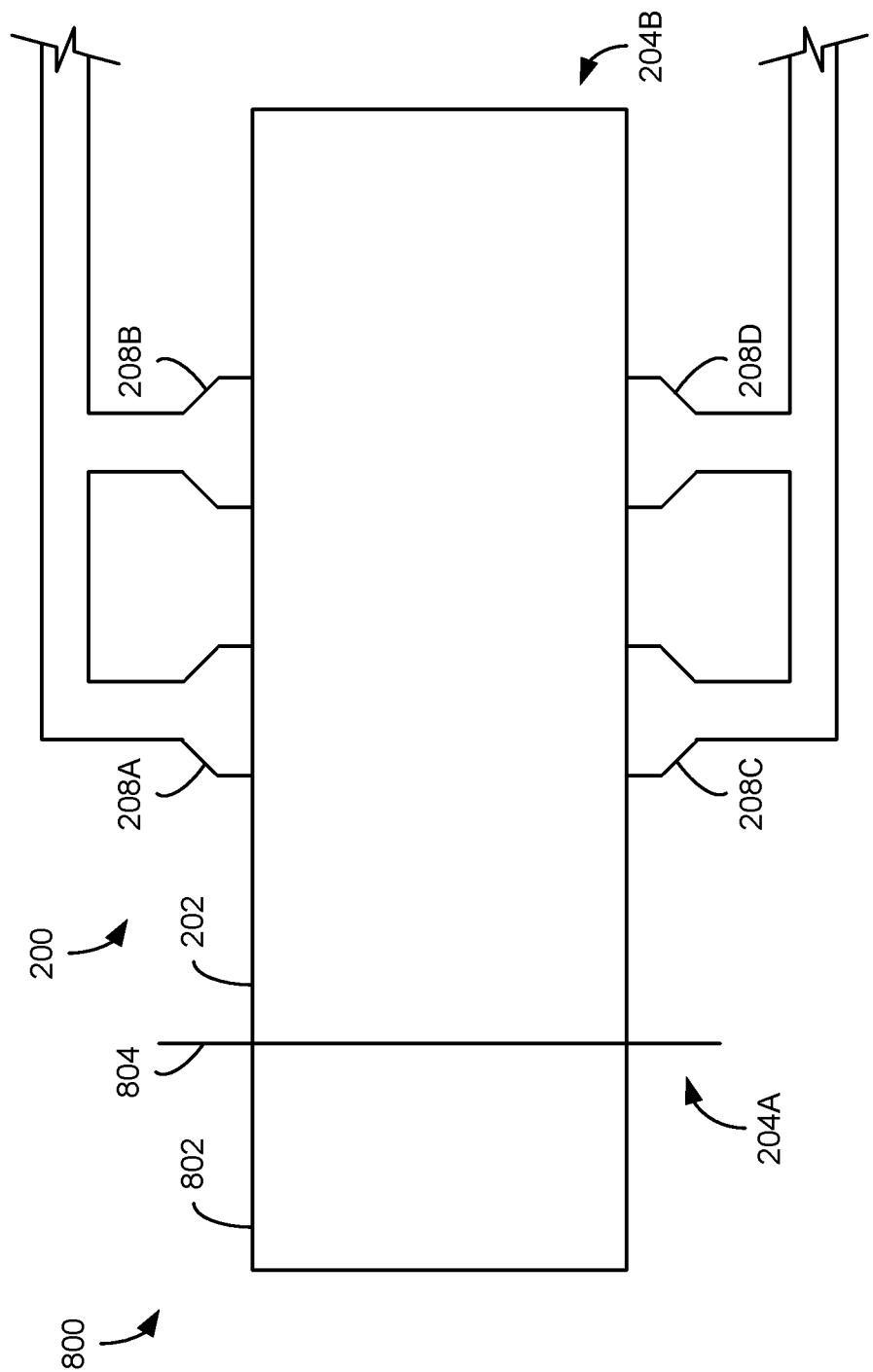
FIG. 8 is a schematic illustration of a first scaled-up electromagnetic heating system including the electromagnetic heating system of FIG. 2 and an upstream vessel.

One example of a combined process unit is shown in FIG. 8. As shown in FIG. 8, the combined processing unit 800 includes the original heating system 200, which includes the vessel 202 and launchers 208A-D, and a new vessel 802 (not to scale), which is attached to the end 204A of the original vessel 202. In operation, all or a portion of the preheating and/or cooling steps can be performed in the new vessel 802 with the appropriate plumbing and nozzles (not shown) connected, while the heating step may be performed in the original vessel 202, which includes the various launchers 208A-D connected thereto. In another example, the cooling step may be performed in the new vessel 802, while the preheating, heating and hold steps may be performed in the original vessel 202. Alternatively, all or part of the preheating step may be performed in the new vessel 802 as well as the cooling step, which would involve the carrier first being positioned in the new vessel 802 for preheating, moved to the original vessel 202 for heating and hold, and then returned to the new vessel 802 for cooling.

The new vessel 802 and the original vessel 202 may or may not be fluidly isolated from one another during processing. For example, in certain implementations an isolation device 804 may be disposed between the new vessel 802 and the original vessel 202. The isolation device 804 may be a gate, valve, door, or similar device that at least partially isolates the new vessel 802 and the original vessel 202. For example, in certain implementations, the isolation device 804 may prevent or reduce the exchange of fluid between the new vessel 802 and the original vessel 202. In other implementations, the isolation device 804 may be configured to selectively allow passage of loaded carriers between the new vessel 802 and the original vessel 202. For example, the isolation device may be a gate, flap, or door that can be selectively opened or closed to permit or prevent passage of carriers.

The carrier may remain stationary in each vessel during the processing steps, or may move within a single vessel or amongst both vessels during all or a portion of one or more of the preheating, heating, holding (if applicable), and cooling steps. The original vessel 202 and/or the new vessel 802 may be configured for and operated at the same or different pressures. In some cases, for example, the pressure of the step or steps performed in the new vessel 802 are at least 5, at least 8, at least 10, or at least 12 psig different than the step or steps performed in the original vessel 202. In other cases, the step or steps performed in the new vessel 802 and those performed in the original vessel 202 are less than 5, less than 3, or less than 2 psig different from one another.

Figure 9:
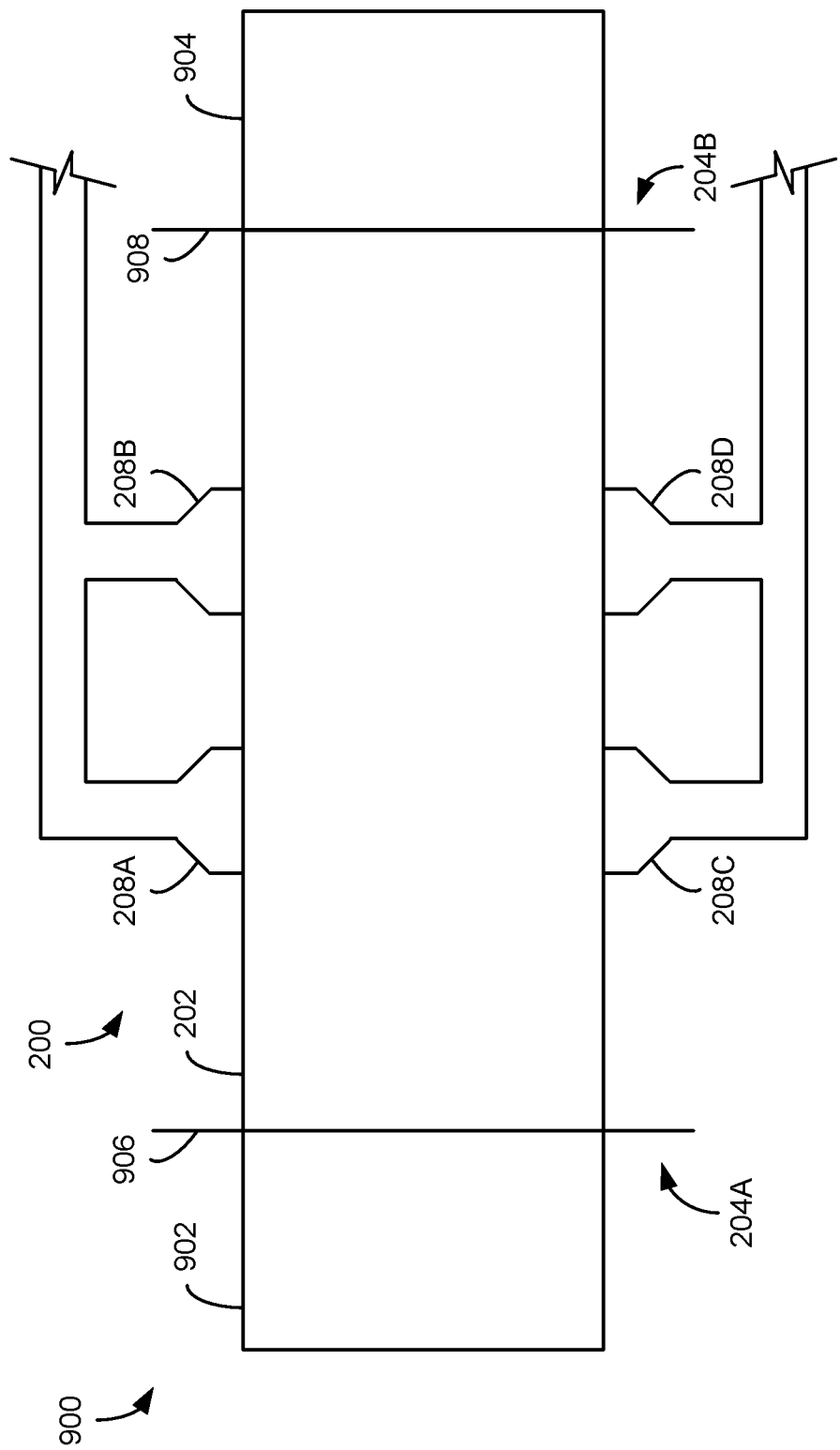
FIG. 9 is a schematic illustration of a second scaled-up electromagnetic heating system including the electromagnetic heating system of FIG. 2 and each of an upstream vessel and a downstream vessel.

Turning now to FIG. 9, another example of a combined processing unit 900 is shown. In the embodiment shown in FIG. 9, two new vessels 902, 904 are added to either side of the electromagnetic heating system 200 and, more specifically, to either side of the vessel 202 of the vessel 202. Again the new vessels 902, 904 are not to scale as compared to the original vessel 202.

In the embodiment shown in FIG. 9, two new vessels are attached to each end of the original heating system 200 and, more specifically, to the ends 204A, 204B of the processing vessel 202. Similar to the combined processing unit 800 of FIG. 8, isolation device 906, 908 may be disposed between the original vessel 202 and each of the new vessels 902, 904. In operation, the combined processing unit shown in FIG. 9 may perform at least a portion of the preheating step in a first of the new vessels 902, the heating step in the original vessel 202, and at least a portion of the cooling step in a second of the new vessels 904. In some cases, it may be advantageous to isolate the vessel 904 in which the cooling is performed in order to minimize temperature change and energy costs. Nozzles and plumbing (not shown) may be connected to the new end vessels 902, 904 as necessary for the arrangement of preheating and cooling operations to be conducted, which may or may not involve both spray and water submersion.

The overall production rate of the system shown in FIGS. 8 and 9 may be larger than the single vessel systems and can, for example, be large lab-scale, pilot scale, or production scale. In some cases, the production rate of these expanded systems can be at least about 15, at least about 20, at least about 25, or at least about 30 packages per minute and/or not more than about 40, not more than about 35, not more than about 30, or not more than about 25 packages per minute. Overall, the volume of the combined processing units shown in FIGS. 8 and 9 can vary but, in certain non-limiting implementations, may be at least about 300, at least about 350, at least about 400, at least about 450, at least about 500, at least about 550, at least about 600, at least about 650, or at least about 700 cubic feet and/or not more than about 1200, not more than about 1100, not more than about 1000, not more than about 900, or not more than about 850 cubic feet.

Subsequently to forming a combined processing unit as shown in FIGS. 8 and 9 (or, in some cases, directly subsequent to operation in a single vessel unit as previously described), the heating system can be further expanded by adding more processing vessels. Again, unlike conventional scale-ups which add more or larger duplicate equipment, the addition of new vessels to the inventive system alters the operation of the vessels, making the process more efficient and less expensive. In some cases, additional preheating, holding, and cooling vessels may be added so that the smaller-scale heating systems described previously with respect to FIGS. 2-9, can be converted to a commercial-scale unit, similar to the one described in U.S. Pat. No. 9,357,590.

Figure 10:
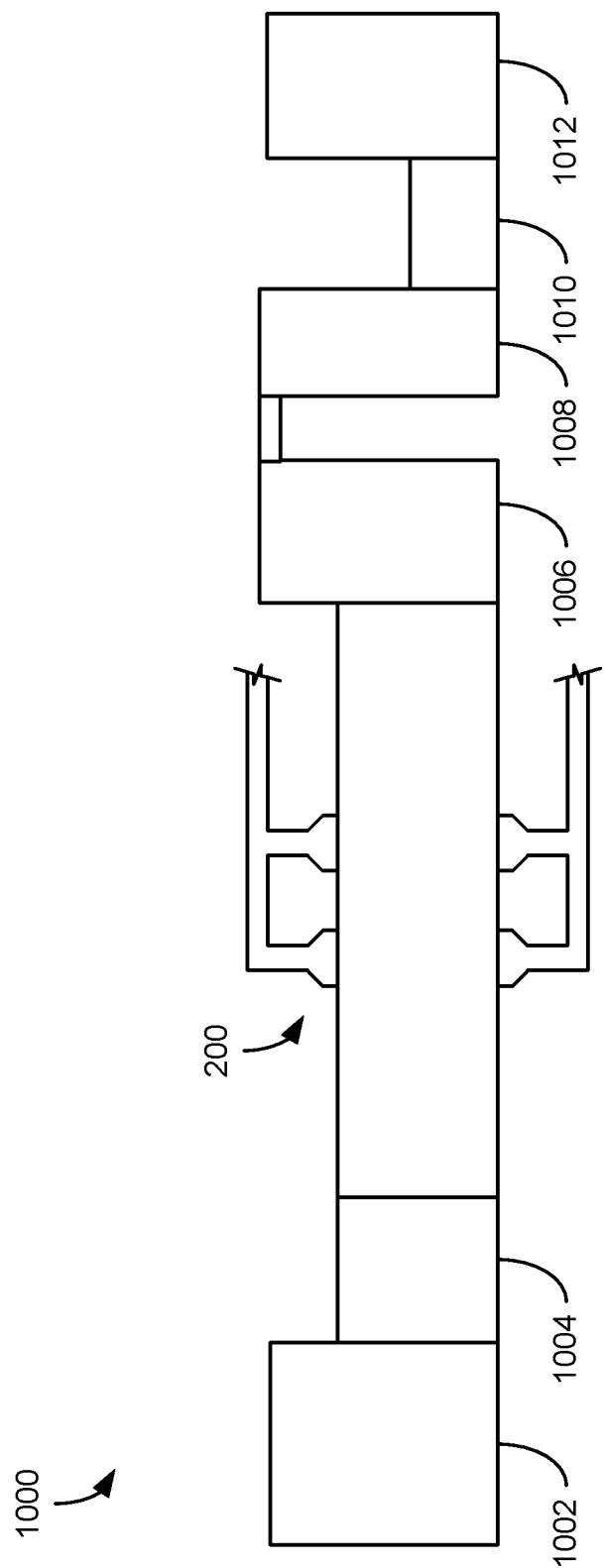
FIG. 10 is a schematic illustration of a third scaled-up electromagnetic heating system including the electromagnetic heating system of FIG. 2 and multiple additional up- and downstream vessels.

One example of a commercial-scale heating system 1000 assembled by attaching several new vessels to an original single-vessel heating system is shown in FIG. 10. As illustrated in FIG. 10, the commercial-scale heating system 1000 includes the original heating system 200 with various additional up- and downstream vessels coupled to the original heating system 200 to expand the functions and capacity of the original heating system 200. In the specific system 1000 illustrated in FIG. 10, for example, the additional vessels include a preheat vessel 1002 and a pressure lock 1004 upstream of the vessel 202 of the heating system 200. The system 1000 further includes a hold vessel 1006, a high pressure cooling vessel 1008, a pressure lock vessel 1010, and a low pressure cooling vessel 1012 downstream of the vessel 202. Accordingly, while the system 200 is configured to provide preheating, heating, holding, and cooling functions, all but the heating function is instead offloaded to the new vessels 1002-1012 of the system 1000. Doing so allows for increased capacity and further customization of the preheating, holding, and cooling functions.

Figure 11:
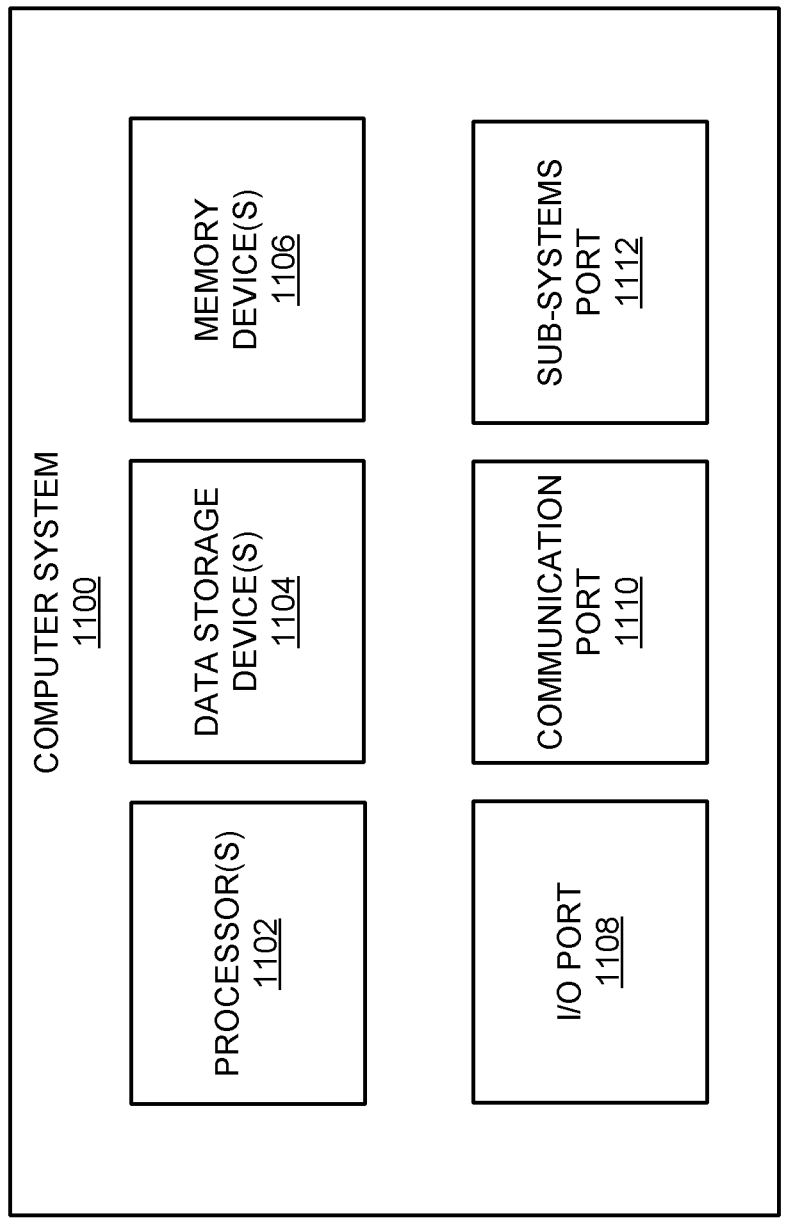
FIG. 11 is a block diagram of an example computer system that may be used in controlling and operating an electromagnetic heating system in accordance with the present disclosure.

Referring to FIG. 11, a schematic illustration of an example computing system 1100 having one or more computing units that may implement various systems, processes, and methods discussed herein is provided. For example, the example computing system 1100 may correspond to, among other things, the control system 150 or (a computing device in communication with or otherwise capable of interacting with the control system 150) of the heating system 100 of FIG. 1. It will be appreciated that specific implementations of these devices may be of differing possible specific computing architectures not all of which are specifically discussed herein but will be understood by those of ordinary skill in the art.

The computer system 1100 may be a computing system capable of executing a computer program product to execute a computer process. Data and program files may be input to computer system 1100, which reads the files and executes the programs therein. Some of the elements of the computer system 1100 are shown in FIG. 11, including one or more hardware processors 1102, one or more data storage devices 1104, one or more memory devices 1108, and/or one or more ports 1108-1112. Additionally, other elements that will be recognized by those skilled in the art may be included in the computing system 1100 but are not explicitly depicted in FIG. 11 or discussed further herein. Various elements of the computer system 1100 may communicate with one another by way of one or more communication buses, point-to-point communication paths, or other communication means not explicitly depicted in FIG. 11.

The processor 1102 may include, for example, a central processing unit (CPU), a microprocessor, a microcontroller, a digital signal processor (DSP), and/or one or more internal levels of cache. There may be one or more processors 1102, such that the processor 1102 comprises a single central-processing unit, or a plurality of processing units capable of executing instructions and performing operations in parallel with each other, commonly referred to as a parallel processing environment.

The computer system 1100 may be a conventional computer, a distributed computer, or any other type of computer, such as one or more external computers made available via a cloud computing architecture. The presently described technology is optionally implemented in software stored on data storage device(s) 1104, stored on memory device(s) 1106, and/or communicated via one or more of the ports 1108-1112, thereby transforming the computer system 1100 in FIG. 11 to a special purpose machine for implementing the operations described herein. Examples of the computer system 1100 include personal computers, terminals, workstations, mobile phones, tablets, laptops, personal computers, multimedia consoles, gaming consoles, set top boxes, and the like.

One or more data storage devices 1104 may include any non-volatile data storage device capable of storing data generated or employed within the computing system 1100, such as computer executable instructions for performing a computer process, which may include instructions of both application programs and an operating system (OS) that manages the various components of the computing system 1100. Data storage devices 1104 may include, without limitation, magnetic disk drives, optical disk drives, solid state drives (SSDs), flash drives, and the like. Data storage devices 1104 may include removable data storage media, non-removable data storage media, and/or external storage devices made available via wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. One or more memory devices 1106 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1104 and/or the memory devices 1106, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1100 includes one or more ports, such as an input/output (I/O) port 1108, a communication port 1110, and a sub-systems port 1112, for communicating with other computing, network, or similar devices. It will be appreciated that the ports 1108-1112 may be combined or separate and that more or fewer ports may be included in the computer system 1100.

The I/O port 1108 may be connected to an I/O device, or other device, by which information is input to or output from the computing system 1100. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1100 via the I/O port 1108. Similarly, the output devices may convert electrical signals received from the computing system 1100 via the I/O port 1108 into signals that may be sensed as output by a human, such as sound, light, and/or touch. The input device may be an alphanumeric input device, including alphanumeric and other keys for communicating information and/or command selections to the processor 1102 via the I/O port 1108. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 1100 via the I/O port 1108. For example, an electrical signal generated within the computing system 1100 may be converted to another type of signal, and/or vice-versa. In one implementation, the environment transducer devices sense characteristics or aspects of an environment local to or remote from the computing device 1100, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example the computing device 1100, such as, physical movement of some object (e.g., a mechanical actuator), heating, or cooling of a substance, adding a chemical substance, and/or the like.

In one implementation, a communication port 1110 is connected to a network by way of which the computer system 1100 may receive network data useful in executing the methods and systems set out herein as well as transmitting information and network configuration changes determined thereby. Stated differently, the communication port 1110 connects the computer system 1100 to one or more communication interface devices configured to transmit and/or receive information between the computing system 1100 and other devices by way of one or more wired or wireless communication networks or connections. Examples of such networks or connections include, without limitation, Universal Serial Bus (USB), Ethernet, WiFi, Bluetooth®, Near Field Communication (NFC), Long-Term Evolution (LTE), and so on. One or more such communication interface devices may be utilized via communication port 1110 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1110 may communicate with an antenna for electromagnetic signal transmission and/or reception.

The computer system 1100 may include a sub-systems port 1112 for communicating with one or more sub-systems, to control an operation of the one or more sub-systems, and to exchange information between the computer system 1100 and the one or more sub-systems. Examples of such sub-systems include, without limitation, imaging systems (such as infrared or other temperat-related imaging systems), motor controllers and systems for controlling aspects of the heating system or associated equipment, battery controllers, fuel cell or other energy storage systems or controls, light systems, environment controls, and the like.

The system set forth in FIG. 11 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

Numerous examples are provided herein to enhance understanding of the present disclosure. A specific set of statements are provided as follows. Such statements are intended merely as examples of potential implementations of the present disclosure and should not be viewed as limiting the scope of the disclosure.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As generally used herein, the terms "about", "substantially", and "approximately" refer to an acceptable degree of error for the quantity measured, given the nature or precision of the measurement. Typical exemplary degrees of error may be within 20%, within 10%, or within 5% of a given value or range of values.

All numerical quantities stated herein are to be understood as being modified in all instances by the term "about" unless otherwise indicated. The numerical quantities disclosed herein are approximate and each numerical value is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example; ranges of "1 to 10" and "between 1 and 10" are intended to include all sub-ranges between and including the recited minimum value of 1 and the recited maximum value of 10.

All percentages and ratios are calculated by weight unless otherwise indicated. All percentages and ratios are calculated based on the total weight of the compound or composition unless otherwise indicated.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined in blocks differently in various implementations of the disclosure or described with different terminology. These and other variations, modifications, additions, and improvements may fall within the scope of the disclosure as defined in the claims that follow.

It should be understood from the foregoing that, while particular implementations have been illustrated and described, various modifications can be made thereto without departing from the spirit and scope of the disclosure as will be apparent to those skilled in the art. Such changes and modifications are within the scope and teachings of this disclosure as defined in the claims appended thereto.

We claim:

1. A method for pasteurizing or sterilizing a plurality of articles in an electromagnetic radiation heating system, said method comprising:
   (a) pasteurizing or sterilizing a first group of articles in a first processing vessel, wherein said pasteurizing or sterilizing includes preheating said first group of articles with a first warming liquid, heating said first group of articles using electromagnetic radiation energy, and cooling said first group of articles with a first cooling liquid;
   (b) attaching a second processing vessel to said first processing vessel to form a combined processing unit; and
   (c) pasteurizing or sterilizing a second group of articles in said combined processing unit, wherein said pasteurizing or sterilizing includes preheating said second group of articles with a second warming liquid, heating said second group of articles using electromagnetic radiation energy, and cooling said second group of articles with a second cooling liquid different from the first cooling liquid,
   wherein, during said pasteurizing or sterilizing of step (c), at least a portion of said heating is performed in said first processing vessel and at least a portion of at least one of said preheating and said cooling is performed in said second processing vessel.

2. The method of claim 1, wherein:
   said attaching of step (b) includes attaching said second processing vessel to one end of said first processing vessel and attaching a third processing vessel to an opposite end of said first processing vessel and
   during said pasteurizing or sterilizing of step (c), at least a portion of said heating is performed in said first processing vessel, at least a portion of said preheating is performed in said second processing vessel, and at least a portion of said cooling is performed in said third processing vessel.

3. The method of claim 1, wherein said first processing vessel comprises a first end segment, a second end segment, and at least one launcher segment between said first and second end segments, wherein said launcher segment comprises pairs of launchers that discharge said electromagnetic radiation energy into said first processing vessel during said heating.

4. The method of claim 3, wherein said first and second end segments do not include any launchers.

5. The method of claim 1, further comprising:
   prior to said pasteurizing or sterilizing of step (a), loading said first group of articles in a first carrier and pasteurizing or sterilizing said first group of articles in said first carrier in step (a); and
   prior to said pasteurizing or sterilizing of step (c), loading said second group of articles into a second carrier and pasteurizing or sterilizing said second group of articles in said second carrier.

6. The method of claim 1, wherein said first processing vessel is at least partially filled with a liquid during at least a portion of said heating of steps (a) and (c).

7. The method of claim 1, wherein the pressure surrounding said first group of articles during each of said preheating, said heating, and said cooling of step (a) is within 10 psig of each of the other of said preheating, said heating, and said cooling of step (a).

8. An electromagnetic heating system for pasteurizing or sterilizing a plurality of articles, said system comprising:
   a processing vessel for receiving a carrier loaded with a plurality of articles, wherein said processing vessel comprises:
      a first end;
      a second end spaced apart from the first end defining a chamber therebetween, at least one of said first and said second ends of said processing vessel including an opening configured for at least one of introducing said carrier into and removing said carrier out of said processing vessel,
      a warm liquid inlet for introducing a warmed liquid into said chamber;
      a cool liquid inlet for introducing a cooled liquid into said chamber;
      a convey line for passing said carrier through at least a portion of said chamber; and
      two launchers for discharging electromagnetic energy into said chamber,
   wherein said processing vessel is configured to be a liquid-filled vessel for each of preheating said articles, heating said articles with electromagnetic energy, and cooling said articles; and
   wherein said processing vessel is configured to be coupled to an additional vessel and, when coupled to the additional vessel, to disable at least one of preheating and cooling functions of the processing vessel.

9. The system of claim 8, wherein the launchers are two of a plurality of launchers for discharging electromagnetic energy into said chamber, the plurality of launchers including more than two launchers.

10. The system of claim 8, wherein the launchers are located on the same side of said processing vessel.

11. The system of claim 8, wherein the launchers are located on opposite sides of said processing vessel.

12. The system of claim 8, wherein said processing vessel further comprises a plurality of nozzles for discharging jets of pressurized liquid into said chamber during at least one of said preheating and said cooling.

13. The system of claim 8, wherein said convey line is configured to transport said articles in opposite first and second horizontal convey directions.

14. The system of claim 8, wherein:
   said processing vessel comprises a first end segment, a second end segment opposite said first end segment, and a launcher segment between said first end segment and said second end segment,
   a portion of said preheating is carried out in said first end segment,
   a portion of said cooling is carried out in said second end segment, and
   a portion of said heating is carried out in said launcher segment.

15. The system of claim 8, wherein said processing vessel includes at least two launcher segments.

16. A method of heating a plurality of articles comprising:
conveying the plurality of articles through each of a first processing vessel and a second processing vessel, wherein:
the first processing vessel includes each of a first preheating zone, a heating zone subsequent to the first preheating zone, and a first cooling zone subsequent to the heating zone, and
the second processing vessel includes one of a second preheating zone and a second cooling zone;
preheating the articles in one of the first preheating zone and the second preheating zone by exposing the articles to a warmed liquid;
while the articles are in the heating zone, directing electromagnetic energy from a plurality of launchers coupled to the first processing vessel into the first processing vessel to heat the articles; and
cooling the articles in one of the first cooling zone and the second cooling zone.

17. The method of claim 16, wherein:
the second processing vessel is coupled to the first processing vessel upstream of the first processing vessel such that the second processing vessel is isolatable from the first processing vessel,
the second processing vessel includes a second preheating zone, and
the step of preheating the articles is performed in the second processing vessel.

18. The method of claim 16, wherein:
the second processing vessel is coupled to the first processing vessel downstream of the first processing vessel such that the second processing vessel is isolatable from the first processing vessel,
the second processing vessel includes a second cooling zone, and
the step of cooling the articles is performed in the second processing vessel.

19. The method of claim 16 further comprising conveying the plurality of articles through a third processing vessel, wherein:
the second processing vessel is coupled to the first processing vessel upstream of the first processing vessel such that the second processing vessel is isolatable from the first processing vessel,
the second processing vessel includes a second preheating zone, and
the step of preheating the articles is performed in the second processing vessel,
the third processing vessel is coupled to the first processing vessel downstream of the first processing vessel such that the third processing vessel is isolatable from the first processing vessel,
the third processing vessel includes a second cooling zone, and the step of cooling the articles is performed in the second processing vessel.

* * * * *